(12) United States Patent
York et al.

(10) Patent No.: US 12,232,806 B2
(45) Date of Patent: Feb. 25, 2025

(54) COMPACT LASER-STEERING END EFFECTOR

(71) Applicant: President and Fellows of Harvard College, Cambridge, MA (US)

(72) Inventors: Peter A. York, Somerville, MA (US); Simon A. Bothner, Etoy (CH); Robert J. Wood, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 45 days.

(21) Appl. No.: 17/769,612

(22) PCT Filed: Oct. 28, 2020

(86) PCT No.: PCT/US2020/057684
§ 371 (c)(1),
(2) Date: Apr. 15, 2022

(87) PCT Pub. No.: WO2021/086928
PCT Pub. Date: May 6, 2021

(65) Prior Publication Data
US 2024/0130784 A1    Apr. 25, 2024
US 2024/0225729 A9    Jul. 11, 2024

Related U.S. Application Data

(60) Provisional application No. 62/926,716, filed on Oct. 28, 2019.

(51) Int. Cl.
*A61B 18/20* (2006.01)
*A61B 34/30* (2016.01)

(52) U.S. Cl.
CPC .............. *A61B 18/20* (2013.01); *A61B 34/30* (2016.02)

(58) Field of Classification Search
CPC ....... A61B 18/20; A61B 18/201; A61B 18/22; A61B 2018/00601; A61B 2018/20359; A61B 34/30; A61B 34/70
See application file for complete search history.

(56) References Cited

U.S. PATENT DOCUMENTS

| 5,586,981 A | 12/1996 | Hu |
| 5,653,706 A | 8/1997 | Zavislan et al. |

(Continued)

FOREIGN PATENT DOCUMENTS

| WO | 2016/060778 A2 | 4/2016 |
| WO | 2017/200991 A2 | 11/2017 |

OTHER PUBLICATIONS

USPTO, International Search Report and Written Opinion for PCT/US20/57684 (Jan. 27, 2021).

(Continued)

*Primary Examiner* — Amanda K Hulbert
(74) *Attorney, Agent, or Firm* — Modern Times Legal; Robert J. Sayre

(57) ABSTRACT

A compact laser-steering end effector includes a frame, at least two active mirrors, and a pair of actuators. The frame has a greatest dimension in a plane orthogonal to a longitudinal axis of no more than 13 mm, and the mirrors are mounted proximate to the distal end of the frame. The actuators are mounted to the frame and configured to respectively change the tilt of the active mirrors relative to the frame. A pathway is provided through the frame to deliver a laser beam to the mirrors, and wherein the mirrors are positioned and configurable via the actuators to reflect the laser beam off of each mirror en route to an external target.

20 Claims, 14 Drawing Sheets

(56) References Cited

U.S. PATENT DOCUMENTS

| | | | |
|---|---|---|---|
| 6,626,895 | B2 | 9/2003 | Frey et al. |
| 9,038,942 | B2 | 5/2015 | Sreetharan et al. |
| 2004/0262507 | A1 | 12/2004 | Kikuchi et al. |
| 2011/0297654 | A1 | 12/2011 | Yoshikawa et al. |
| 2012/0302828 | A1 | 11/2012 | Toledo-Crow et al. |
| 2013/0059264 | A1 | 3/2013 | Monty |
| 2019/0255660 | A1 | 8/2019 | Mori |

OTHER PUBLICATIONS

S. Patel, et al., "Endoscopic laser scalpel for head and neck cancer surgery," in Photonic Therapeutics and Diagnostics VIII, vol. 8207, International Society for Optics and Photonics 82071S (2012).

O. Ferhanoglu, et al., "A 5-mm piezo-scanning fiber device for high speed ultrafast laser microsurgery," Biomedical Optics Express, vol. 5, No. 7, 2023-2036 (2014).

A. Acemoglu, et al., "Design and control of a magnetic laser scanner for endoscopic microsurgeries," IEEE/ASME Transactions on Mechatronics (2019).

R. Renevier, et al., "Endoscopic laser surgery: design, modeling and control," IEEE/ASME Transactions on Mechatronics, vol. 22, No. 1, 99-106 (2017).

P. S. Sreetharan, et al., "Monolithic fabrication of millimeter-scale machines," Journal of Micromechanics and Microengineering, vol. 22, No. 5, 055027 (2012).

R. Wood, "The First Takeoff of a Biologically Inspired At-Scale Robotic Insect," IEEE Transactions on Robotics, 24(2), 341 (2008).

N. T. Jafferis, M. J. Smith, and R. J. Wood, "Design and manufacturing rules for maximizing the performance of polycrystalline piezoelectric bending actuators," Smart Materials and Structures, vol. 24, No. 6, p. 065023 (2015).

European Patent Office, extended European Search Report, issued in the examination of EP App. No. 20883591.8 (Oct. 26, 2023).

COMPACT LASER-STEERING END EFFECTOR

BACKGROUND

The discussion of the background state of the art, discussed below, may reflect hindsight gained from the disclosed invention(s); and these characterizations are not necessarily admitted to be prior art.

Over 30,000 people in the United States were diagnosed in 2018 with a cancer of the pharynx or larynx, resulting in 6,000 deaths. These cancers are notable for their deleterious effect on quality of life; their symptoms, including dysphagia and voice impairment, often lead to depression and social isolation, and curative treatments often exacerbate these functional maladies. Incidence, historically driven by the smoking of tobacco, is increasingly driven by human papillomavirus, resulting in a historically young patient population even more acutely concerned with long-term functional outcomes.

Thus, there is significant need for curative treatment methods for these cancers that enable post-treatment organ function. Partial or full organ removal via open surgery represents one extreme, presenting the near guarantee of excellent oncological results at the expense of functional outcomes. Non-operative methods, including induction chemotherapy, intensity-modulated radiotherapy, and concurrent chemotherapy with radiotherapy, offer better functional outcomes than open surgery while achieving good oncological results. Such techniques are currently recommended for most laryngeal cancers. Within the last two decades, however, the long-term morbidity and functional impairment associated with radiotherapy have led otolaryngologists to reexamine surgical techniques. Minimally invasive methods have been of particular interest, with a view toward greater preservation of healthy tissue and associated improvements in post-operative organ function relative to open surgery.

Transoral laser microsurgery (TLM) is the most-mature minimally invasive approach. In TLM, a carbon dioxide laser is coupled to a surgical microscope and aimed through a laryngoscope, which provides line-of-sight access to the upper airway. The surgeon uses manual tools inserted through the laryngoscope to retract the lesion and uses a micromanipulator on the microscope to steer the laser beam to resect the diseased tissue. In advanced systems, the micromanipulator is motorized, allowing the surgeon to direct the laser along predetermined arcs and lines at precisely controlled speeds, resulting in very-high-quality incisions. The most significant limitation of TLM is its line-of-sight constraint, which restricts both visualization and exposure. Moreover, the long, narrow laryngoscope makes the manual manipulation of tools required for retraction and suturing difficult.

To address these shortcomings, transoral robotic surgery (TORS) was developed in the mid-2000s. In TORS, flexible or wristed robotic manipulators are used in conjunction with endoscopic vision systems, providing superior visualization and tissue manipulability at the surgical site. The DA VINCI multi-port and DA VINCI single-port systems (from Intuitive Surgical Inc, Sunnyvale, CA) and the FLEX robotic system (from Medrobotics, Raynham, MA, USA) are currently in clinical use.

However, in one key respect, TORS remains deficient to TLM; in TORS, electrocautery is primarily employed for resection, which leads to greater post-operative pain and longer recovery times than is experienced with similar procedures conducted with TLM. With the recent development of hollow-core fibers capable of delivering carbon-dioxide lasers through flexible instruments, the use of lasers in TORS is expected to increase, which should mitigate this problem to some degree. Fiber-based lasers, however, are held and manipulated by robotic tools, and thus lack the spatial repeatability, precision, and speed of free-beam scanning systems. This implies that incision quality suffers relative to the free-beam systems used for TLM. Free-beam systems have the additional benefit of leaving the surgical site clear for exposure and visualization of margins.

A number of prototype endoscopic devices have been developed for minimally invasive laser scanning tasks, each with a different approach to the challenging design problem. In S. Patel, et al., "Endoscopic laser scalpel for head and neck cancer surgery," in Photonic Therapeutics and Diagnostics VIII, Vol. 8207, International Society for Optics and Photonics 82071S (2012), DC motor-driven Risley prisms were used as the beam-steering method, which allows for easy-to-implement control schemes, but scanning speed is very limited (2 Hz). In O. Ferhanoglu, et al., "A 5-mm piezo-scanning fiber device for high speed ultrafast laser microsurgery," Biomedical Optics Express, Vol. 5, No. 7, 2023-2036 (2014), piezoelectric actuators are used to directly bend an optical fiber, achieving a large bandwidth (1 kHz) in a thin device profile (5-mm diameter); but the field of view (200×200 μm) suffered as a result. In A. Acemoglu, et al., "Design and control of a magnetic laser scanner for endoscopic microsurgeries," IEEE/ASME Transactions on Mechatronics (2019), electromagnets are used to bend a fiber, which increased the range of motion to 3×3 mm but, in doing so, sacrificed bandwidth (15 Hz). Lastly, as described in R. Renevier, et al., "Endoscopic laser surgery: design, modeling and control," IEEE/ASME Transactions on Mechatronics, Vol. 22, No. 1, 99-106 (2017), the FEMTO-ST Institute developed a system that uses off-the-shelf piezoelectric linear actuators to articulate a silicon mirror held on a tip-tilt stage, which achieves a 20×20 mm field of view, albeit at a low scanning speed (17 Hz).

SUMMARY

A compact laser-steering end effector and a method for using the end effector, particularly, for surgery, are described herein, where various embodiments of the apparatus and methods may include some or all of the elements, features and steps described below.

A compact laser-steering end effector includes a frame, at least two active mirrors, and a pair of actuators. The frame has a greatest dimension in a plane orthogonal to a longitudinal axis of no more than 13 mm, and the mirrors are mounted proximate to the distal end of the frame (i.e., closer to the distal end than they are to the proximate end of the frame. The actuators are mounted to the frame and configured to respectively change the tilt of the active mirrors relative to the frame. A pathway is provided through the frame to deliver a laser beam to the mirrors, and wherein the mirrors are positioned and configurable via the actuators to reflect the laser beam off of each mirror en route to an external target.

In a method for robotic laser steering, a laser beam is generated and directed into a proximal end of an end effector to a region proximate a distal end of the end effector. The laser beam is reflected in the region proximate the distal end of the end effector with at least two active mirrors, and actuators are used to change the tilt orientation of the at least two active mirrors to displace the laser beam across a target.

The apparatus and methods discussed herein can capture the benefits of both TLM and TORS in a laser scanning system that operates at the end of a robot manipulator. The apparatus and methods can enable more-precise incisions, and, correspondingly, less tissue damage than is possible with existing laser or electrocautery tools. Moreover, moving the laser fiber inside the robot manipulator can relax some of the constraints on the fiber's design and use, which is advantageous considering that currently available $CO_2$-laser fibers are expensive (around US$1,000) and single-use. Below, we describe a prototype device for enabling this TLM/TORS hybrid paradigm.

Minimally invasive surgical methods that facilitate greater preservation of healthy tissue have recently emerged, but they are still limited in important ways. Herein, we describe a device that can combine the following advantages of the two existing primary minimally invasive approaches: (a) the high-quality incision and reduced post-operative pain achievable with transoral laser microsurgery and (b) the superior visualization and tissue manipulability afforded by transoral robotic surgery. In a particular exemplification, an 11-mm-diameter device connects to a fiber optic laser source and directs a focused laser beam across a 18-x-10-mm plane with controllable trajectories at speeds up to 7 m/s.

By combining the strengths of TORS and TLM, this approach has promise to improve the quality of care for, e.g., pharyngeal and laryngeal cancers. It can allow for better access and exposure than with TLM, alone, and higher incision quality than with TORS, alone, the net result of which can be more streamlined procedures for surgeons and better functional outcomes for patients. In other applications, this approach can be used for performing laser-assisted cardiac ablation, laser-assisted surgery of gastrointestinal tract, laser-assisted abdominal surgery, or laser-assisted transnasal skull base surgery.

The end effectors described herein can actuate precisely at high speeds, enabling important new ways of robotically interacting with living tissue. In particular, the end effector can be incorporated in a microrobotic device to enable the dexterous control of laser energy in minimally invasive surgery. The high-bandwidth distal actuation enabled with these devices and methods can be integrated with existing surgical tools to precisely control the position of a fiber-delivered laser. The fabrication and modular assembly approaches described herein enable the creation of a device significantly smaller with higher bandwidth than the current state of the art while achieving a range of motion similar to existing tools. For example, the device can have a diameter of no more than 6 mm in diameter and 16 mm in length and is capable of focusing and steering a fiber-delivered laser bean at high speed (e.g., 1.2 kHz bandwidth) over a large range (e.g., +/−10° in both of two axes) with excellent static repeatability (e.g., +/−200 μm). This approach enables greater control over energy delivery in surgery than is possible with existing rigid and cable-driven tools because the laser speed and, thus, duration of energy application can be precisely controlled over a wide range. This approach to dexterous energy delivery can be deployed in diverse surgical arenas in which controllable energy is needed in a confined space.

BRIEF DESCRIPTION OF THE DRAWINGS

FIG. 13 shows the first mirror linkage 38, while FIG. 14 shows the second mirror linkage 38. A first set of solid lines 71 depict the effective links of the crank slider, the dotted line 73 represents the axis of rotation of the crank, and the second set of solid lines 75 show the physical part bent backwards to facilitate the assembly of the linkages 38. The joints are represented by black circles 77, and the slider translation and crank rotation are represented by the dotted black trajectories 79.

FIG. 16 shows individual layers of rigid material 60, flexible material 62, and adhesive material 64 cut using laser micromachining.

FIG. 17 shows layers 60 and 62 aligned on pins 68 and laminated using heat and pressure on a lamination plate 66.

In FIG. 18, additional laser micromachining reveals the structure of the linkage 38 of the first instantiation of the end effector.

In FIG. 19, after the assembly tabs are released, the linkage structure 38 is partially deployed.

In FIG. 20, a 3D-printed assembly jig 70 is used to bend the linkage arms to their desired positions.

In FIG. 21, the final tabs are released; and the linkages 38 are ready to be integrated with the rest of the device.

Figure 1:
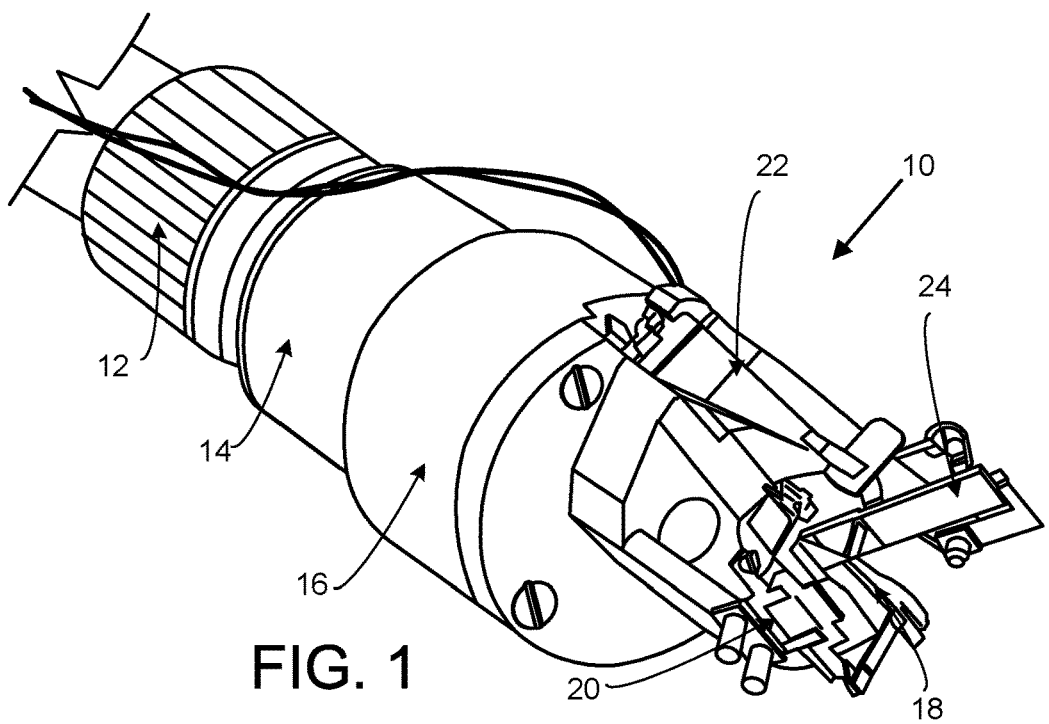
FIG. 1 shows a first instantiation of an end effector 10 of a laser-scanning system for use in transoral robotic surgery. The end effector 10 receives a fiber input and steers a focused spot on the surgical plane.

In the accompanying drawings, like reference characters refer to the same or similar parts throughout the different views. The drawings are not necessarily to scale; instead, an emphasis is placed upon illustrating particular principles in the exemplifications discussed below. For any drawings that include text (words, reference characters, and/or numbers), alternative versions of the drawings without the text are to be understood as being part of this disclosure; and formal replacement drawings without such text may be substituted therefor.

DETAILED DESCRIPTION

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

Unless otherwise herein defined, used or characterized, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially (though not perfectly) pure, as practical and imperfect realities may apply; e.g., the potential presence of at least trace impurities (e.g., at less than 1 or 2%) can be understood as being within the scope of the description. Likewise, if a particular shape is referenced, the shape is intended to include imperfect variations from ideal shapes, e.g., due to manufacturing tolerances. Percentages or concentrations expressed herein can be in terms of weight or volume. Processes, procedures and phenomena described below can occur at ambient pressure (e.g., about 50-120 kPa—for example, about 90-110 kPa) and temperature (e.g., −20 to 50° C.—for example, about 10-35° C.) unless otherwise specified.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments.

Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly. The term, "about," can mean within ±10% of the value recited. In addition, where a range of values is provided, each sub-range and each individual value between the upper and lower ends of the range is contemplated and therefore disclosed.

Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as those introduced with the articles, "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

Additionally, the various components identified herein can be provided in an assembled and finished form; or some or all of the components can be packaged together and marketed as a kit with instructions (e.g., in written, video or audio form) for assembly and/or modification by a customer to produce a finished product.

In minimally invasive surgery, access is gained to internal anatomy through natural orifices or small external incisions. It encompasses diverse practices such as the catheter delivery of stents (angioplasty), flexible endoscopy of the gastrointestinal tract, laparoscopic treatment of abdominal diseases, and trans-nasal operation at the skull base for neurological conditions. Common to many of these procedures is the need for wristed articulation at the distal ends of tools for manipulating tissue and visualizing the surgical site. The need for this articulation was an important motivation for introducing robotics into minimally invasive surgery, which remains a vibrant area of research and development today.

Proximally actuated cable transmission approaches are pre-eminent for achieving wristed articulation due to the significant size constraints imposed by the method of access and size of the anatomy. Nevertheless, the downsides of cable actuation are well known: output force is limited by allowable cable tension, and bandwidth is limited by series elasticity and the mass and elasticity of backlash-inhibiting preloading components. These limitations have motivated significant research effort into creating new distal dexterity mechanisms actuated through other means, such as shape-memory actuators, pneumatic fluids, or flexible rods that achieve dexterity without the limitations of cable actuation.

Herein, we focus on a subset of the tools used in minimally invasive surgery—those used for energy delivery. Common surgical energy sources include monopolar and bipolar radio-frequency electric current (electrosurgery), thermal cautery (direct current heating), ultrasonic vibrations, argon beam coagulation (argon assists the conduction of radio-frequency current), and laser. These tools are essential to the surgical workflow because they enable the cutting, coagulation, desiccation, and carbonization of tissue deep inside the body. The different energy sources ultimately have the same effect—denaturizing proteins through the heating of tissue. Moreover, these energy sources are at present used in a similar way. Specifically, the energy sources are brought close (e.g., within a few millimeters) to the tissue, and energy is delivered directly from the electrode or fiber to the anatomy being treated.

However, a significantly more sophistical approach is possible when it comes to delivering laser energy. Though current laser-based tools are used in the static, close-contact way, a dynamic approach could be employed using a miniature laser galvanometer as a wrist to steer the laser energy. Because lasers can be focused and steered using low-inertia optical components, high-bandwidth distal actuation can be used to control the laser position, which yields the same benefits that robotic wrists grant to mechanical end effectors (i.e., the ability to work around corners and navigate obstacles) while achieving additional capability to precisely control the speed of the laser on the tissue over a wide range, which is important because laser speed strongly affects the duration of laser irradiation, a critical determinant of the quality of laser/tissue interaction in terms of the incision depth, spread of thermal damage, and hemostatic effect.

The challenge to creating this type of robotic device is the opto-electrical-mechanical complexity needed in a small package. Device diameter is a key constraint and depends on the type of surgical tool being used; a sampling of commonly used tools shows a range of different sizes: colonoscopes ranging from 9.7 to 14.8 mm (e.g., PCF-PH190I/L and CF-FH260AZI/L colonoscopes from Olympus Medical Systems), laparoscopic tools either 5 or 8 mm (e.g., da Vinci SP from Intuitive Surgical), rhinolaryngoscopes for transnasal access ranging from 2.6 to 4.9 mm (e.g., ENF-V3 and ENF-VT3 rhinolaryngoscopes from Olympus Medical systems), and cardiac catheters ranging from 2.67 to 3.33 mm, (e.g., AcuNav cathethers from Biosense Webster).

Utilizing breakthroughs in millimeter-scale design and fabrication, we show how to integrate microrobotic laser beam steering with a subset of those tools. Our approach builds on recent advances at the intersection of robotics and medicine that leverage millimeter-scale actuators and sensors for more precise control of tools and manipulation of tissue. An exemplification of our laser-steering solution is 6 mm in diameter and can thus be seamlessly integrated into existing workflows in flexible gastroenterology and single-port surgery—settings for which adapting traditional tools is difficult and lasers are of particular interest.

The end effector with microrobotic laser beam steering can be integrated with a surgical tool, such as a colonoscope (Olympus CF-100L). The end effector can be attached externally to the surgical tool or, because it is small enough, can be internally integrated into a special-purpose flexible scope. The device can be 16 mm in length and can possess the ability to steer a focused laser beam through over +/−10° on two orthogonal axes with a 1.2 kHz mechanical bandwidth.

The performance we achieve represents substantial improvement over the state of the art, which tend to be bulky and slow. These solutions are all larger than a centimeter in diameter and longer than two centimeters in length. While these devices achieve similar ranges of motion to our device, speed is sacrificed by the actuators and the mechanisms they employ. In contrast, our approach employs piezoelectric bending actuators acting through flexure-based transmissions to generate the rotational motion of low-inertia mirrors. In this way, we achieve mechanical bandwidth one to two orders of magnitude greater than the state of the art and excellent repeatability (i.e., precision).

We herein describe our substantial advancements in design, fabrication, and control that allow us to surpass the performance of state-of-the-art devices. These include general principles for building miniature laser galvanometers as well as specific design details for our device. In exemplifications of our approach, we separate the device into modules—lenses, actuators, mirrors, etc.—that can be individually validated and then mounted on disks and assembled onto a railed superstructure, which serves as a common mechanical ground, thereby minimizing the number of assembly features and facilitating alignment of critical components. For fabrication, we can use lamination techniques for making miniature compliant mechanisms that allow us to generate large-angle mirror rotations without sacrificing miniaturization. For control, a low-dimensional hysteresis compensation scheme can be used that corrects for the hysteresis in the piezoelectric bending actuators and intermediate mechanisms.

Figure 2:
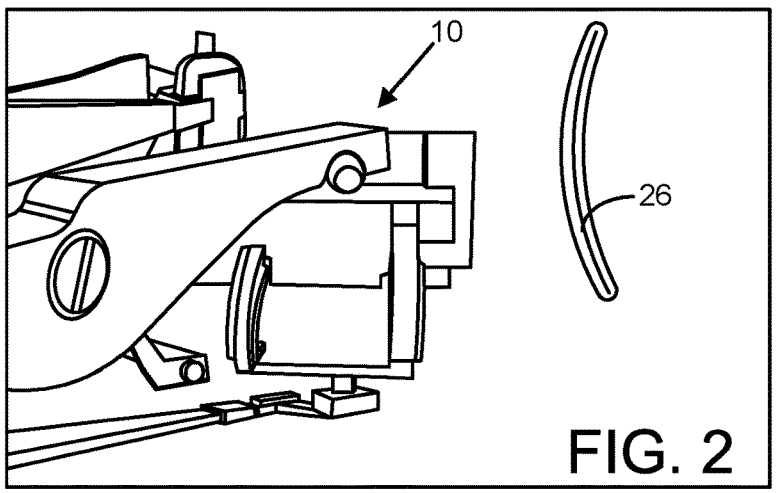
FIGS. 2 and 3 are long-exposure photographs demonstrating typical cut profiles used in laser-based tissue resection using end effector design of FIG. 1.
Figure 3:
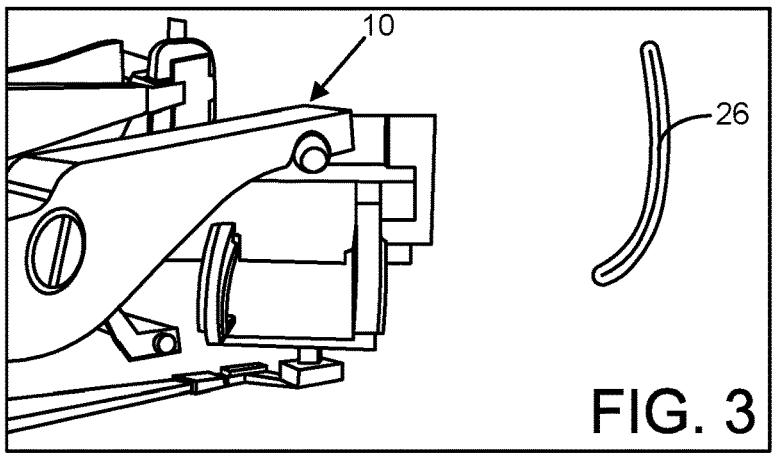
Figure 4:
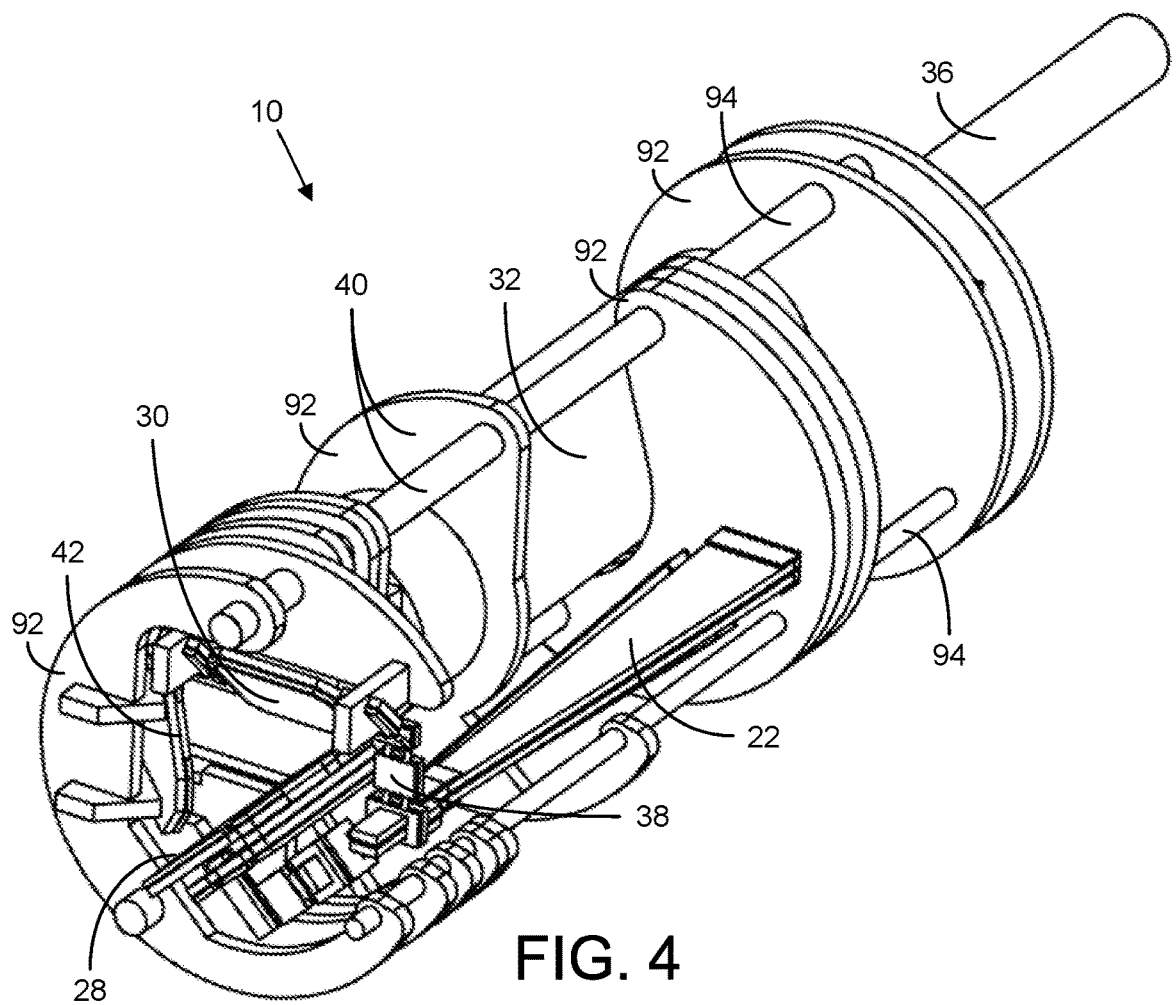
FIG. 4 is a perspective view of a second instantiation of a compact laser-steering end effector 10 for robotic surgery.
Figure 5:
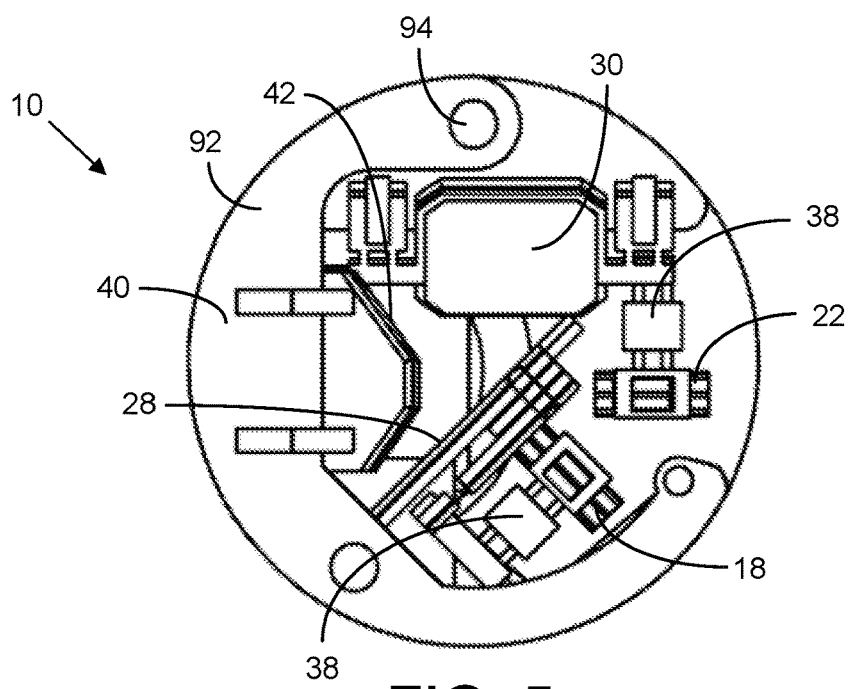
FIG. 5 is an end view of the compact laser-steering end effector 10 for robotic surgery shown in FIG. 4.
Figure 6:
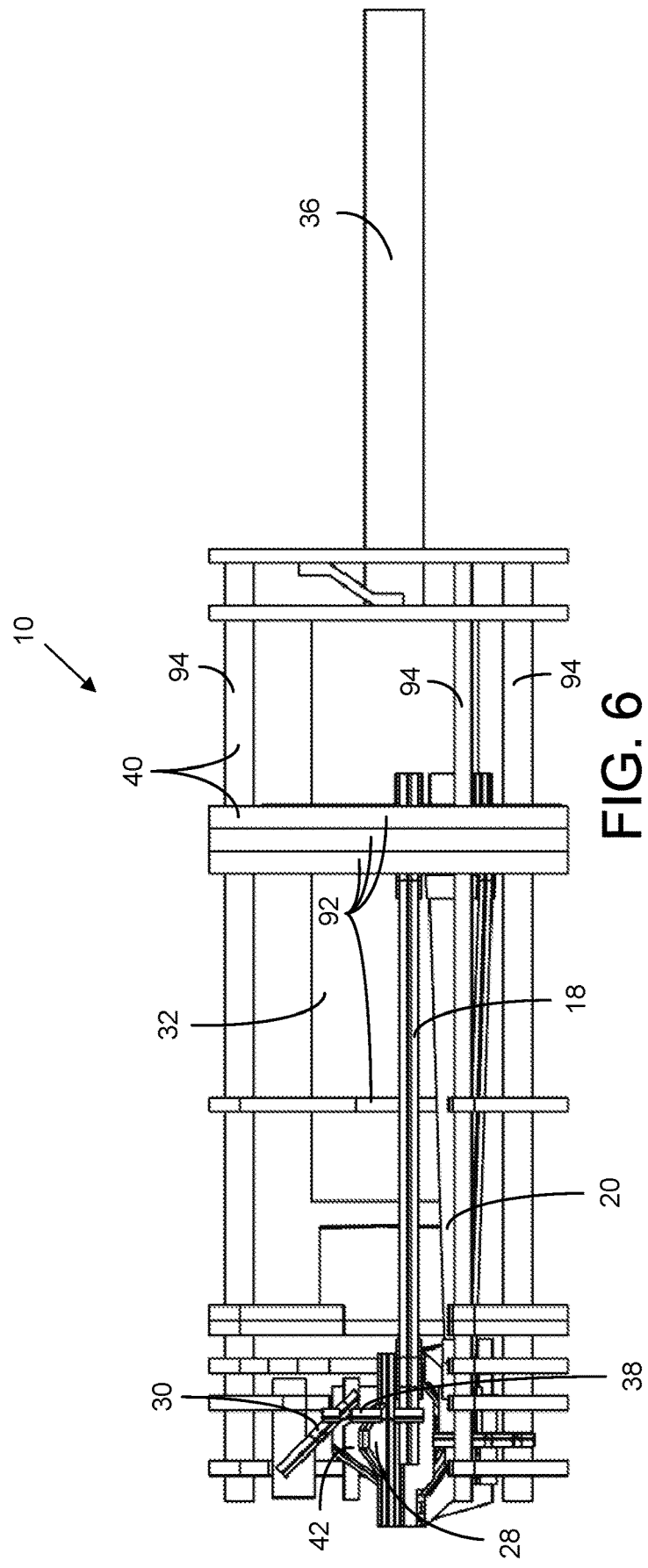
FIG. 6 is a side view of the compact laser-steering end effector 10 for robotic surgery shown in FIGS. 4 and 5.
Figure 7:
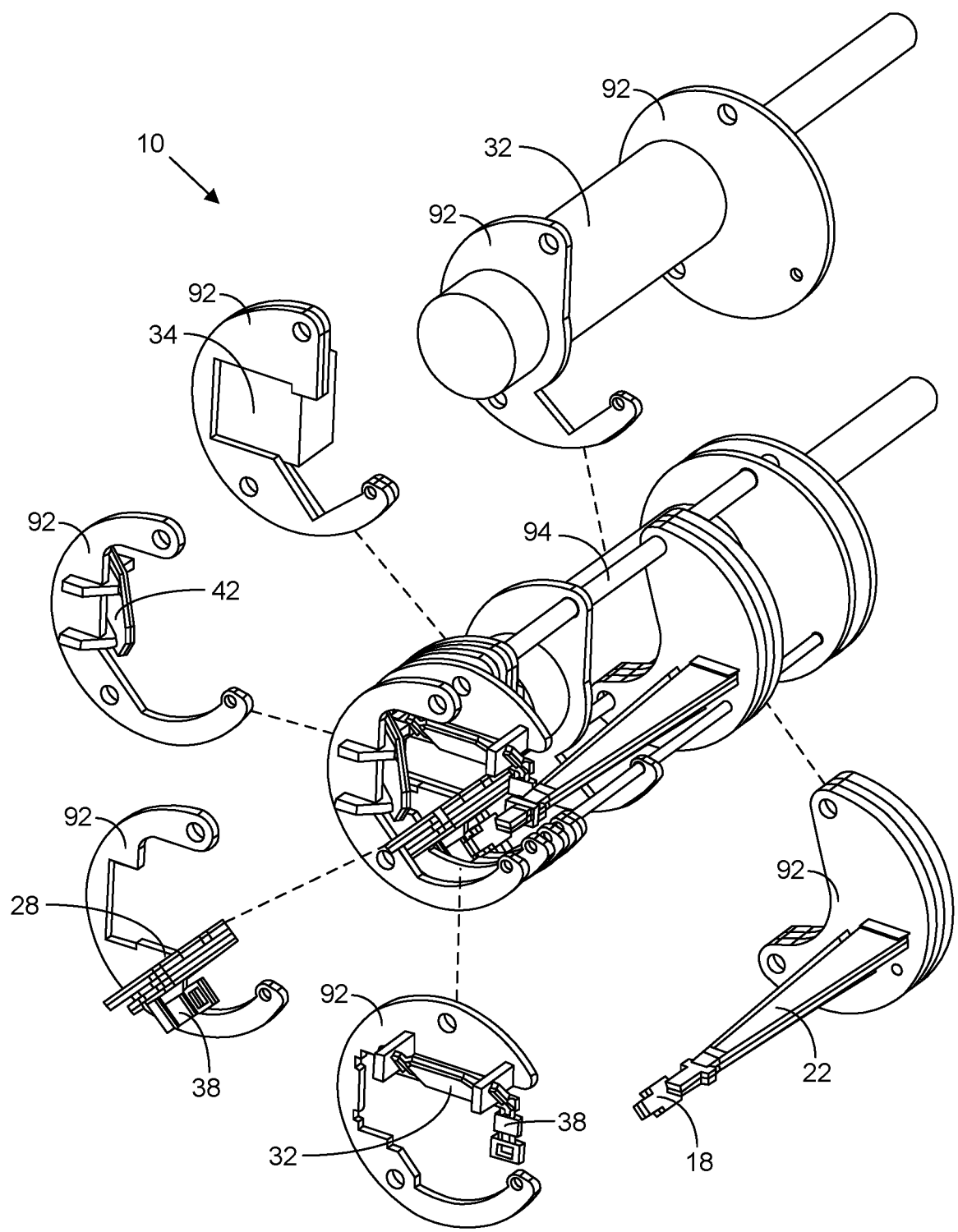
FIG. 7 is a perspective view of the compact laser-steering end effector 10 for robotic surgery shown in FIGS. 4-6 with exploded views of various parts of the end effector 10.
Figure 8:
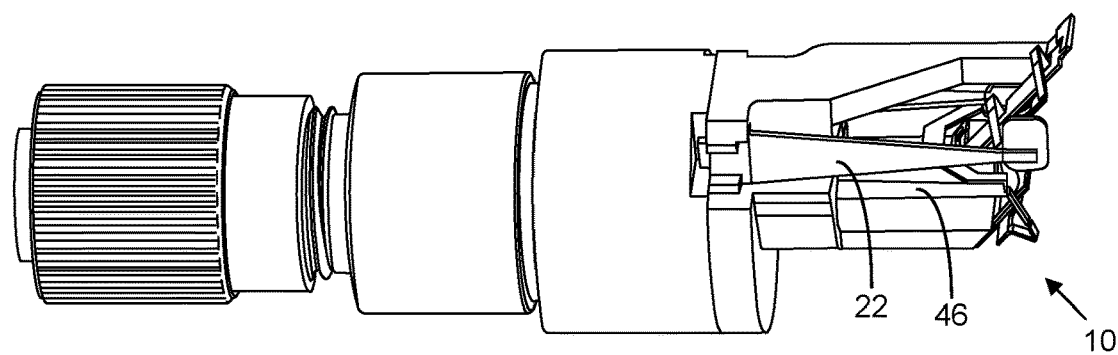
FIG. 8 is a perspective drawing of the first instantiation of the laser-scanning end effector 10 defining the location of key subsystems.
Figure 9:
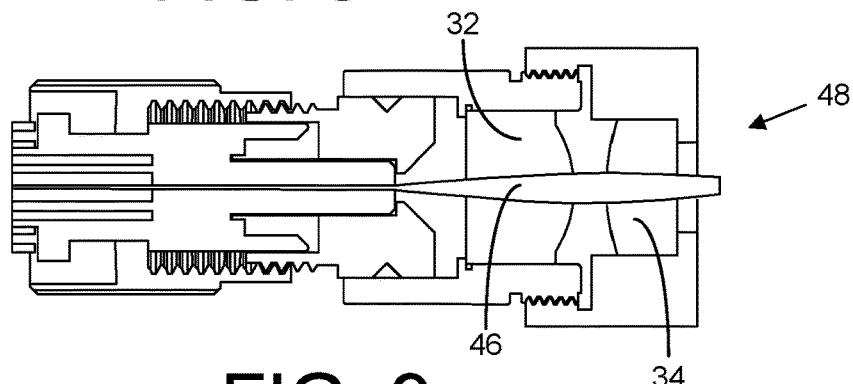
FIG. 9 shows the optical subsystem 48 of the end effector 10 of FIG. 8. The optical subsystem 48 connects a fiber optic source to the laser scanner.
Figure 10:
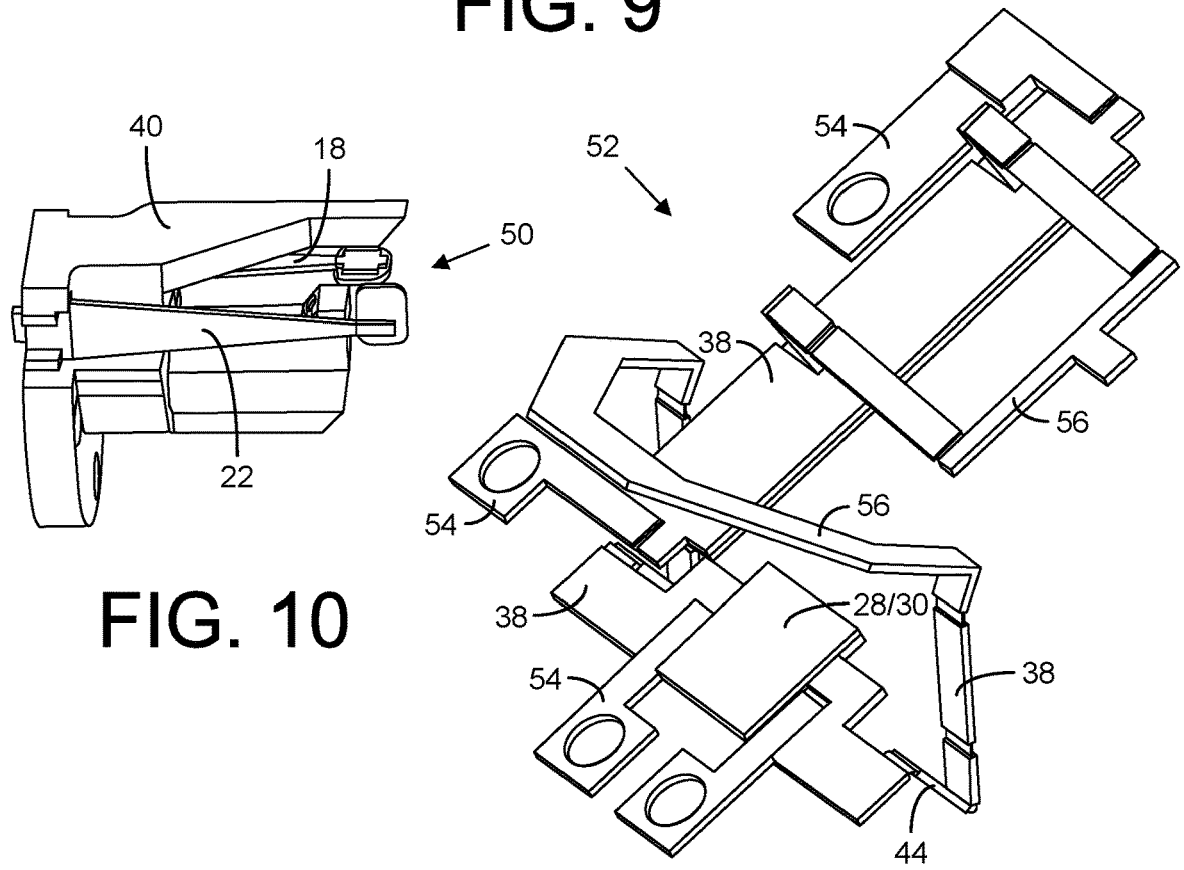
FIG. 10 shows the actuation subsystem 50 of the end effector 10 of FIG. 8, including piezoelectric bending actuators 18 and 22 and a rigid mechanical frame (base) 40 that aligns the optics with the rest of the device.

A laser-scanning system for use in transoral robotic surgery and including a compact laser-steering end effector 10 is shown in FIG. 1. The device receives a laser input from an optical fiber 12 and steers a focused spot on the surgical plane. The device can include two lasers, including a lower-powered navigating laser to illuminate internal cavities to assist with visualization and navigating the end effector to desired positions as well as a higher-powered surgical laser for cutting tissue. The laser passes from the optical fiber 12 through a collimator 14 to a mechanical structure 16 including a first-linkage actuator 18 configured to displace a first-linkage-and-mirror assembly 20 as well as a second-linkage actuator 22 configured to displace a second-linkage-and-mirror assembly 24. FIGS. 2 and 3 are long-exposure photographs demonstrating typical cut profiles used in laser-based tissue resection.

Figure 11:
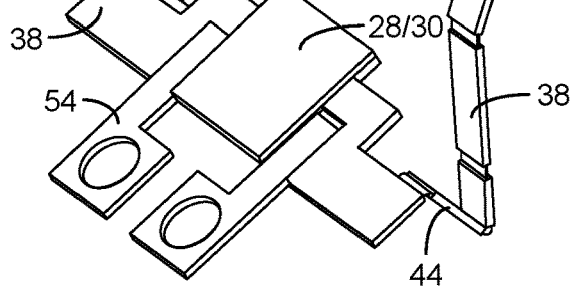
FIG. 11 shows the mirror subsystem 52 of the end effector 10, including a motion transmission linkage 38 and a flat active mirror 28/30.

As shown in FIGS. 4-11, recently developed microfabrication techniques [as described in P. S. Sreetharan, et al., "Monolithic fabrication of millimeter-scale machines," Journal of Micromechanics and Microengineering, Vol. 22, No. 5, 055027 (2012)] can be employed to create miniature mechanical transmission linkages 38 that convert the quasi-linear motions of high-bandwidth piezoelectric bending actuators 18 and 22 into rotational motions that are used to orient mirrors 28 and 30, which receive the laser beam following reflection of the beam from a fixed mirror 42. Exemplifications of our device include two such actuator-transmission-mirror combinations, situated orthogonally, such that the two actuation inputs from the actuators 18 and 22 correspond to ablation in orthogonal directions on the target tissue. Light is transmitted to the laser scanner using an optical fiber in a laser-injection conduit 36, where the output is fed, as a free beam (no longer contained in a fiber) into a gradient-index collimating lens 32 and miniature plano-convex focusing lens 34 assembly. The free and focused beam is then steered by rotating the two active mirrors 28 and 30 using crank-slider transmissions to convert the linear actuator movement from the actuation subsystem 50 (FIG. 10) to the desired rotational movement. The scanning frame 40 (including rigid disk platforms 92 slidably mounted onto rigid rods 94) provides a mechanical ground for the actuators 18 and 22 and the transmissions 38, as well as guaranteeing precise alignment between the optical subsystem 48 (FIG. 9) and the mirror subsystem 52 (FIG. 11).

As shown in FIGS. 4-7, the end effector 10 can include two actuators 18 and 22 in the form of piezoelectric bimorph cantilevers 18 and 22, as described in U.S. Pat. No. 9,038,942 B2 (Harvard).

The piezoelectric bimorph cantilevers 18 and 22 can be fabricated via a smart-composite-microstructure fabrication technique, as described in R. Wood, "The First Takeoff of a Biologically Inspired At-Scale Robotic Insect," IEEE Transactions on Robotics, 24(2), 341 (2008). First, individual lamina [e.g., $PbZrTiO_3$ (PZT)-5H piezoelectric layers and a M60J carbon fiber/cyanate ester resin prepreg layer] can be laser-micro-machined into desired link shapes. These layers can then be stacked and aligned and put through a controlled cure cycle that regulates temperature, pressure, and time of cure. Each of the resulting actuators 18 and 22 is fixed to the frame 40 (comprising a plurality of rigid plates 92 mounted along a plurality of rigid rods 94) proximally and to a passive transmission linkage 38 distally, wherein the passive linkage 38 provides a transmission structure for converting the bending displacement of the cantilever actuator 18/22 to adjust the tilt of one of the active mirrors 28/30 so as to steer the reflection of the laser toward a desired target. A voltage source is also coupled with the actuator 18/22, wherein application of a voltage to either of the piezoelectric layers will cause the actuator 18/22 to bend.

The coupling of one of the passage transmission linkages 38 to one of the active mirrors 28/30 is shown in FIG. 11. The mirror 28/30 is mounted to pivot about a rotation pin 44 that is mounted in a rigid mount extending from a mechanical-ground plate 54 in the frame so that rotation of the rotation pin 44 in the rigid mount via displacement of the passive linkage 38 produces a change in in the tilt angle of the active mirror 28/30.

Design requirements are derived from the prospective surgical environment. We choose a target field of view of 10×20 mm, in accordance with the nominal size of the vocal folds. In order to leave room for retraction tools, visualization, and illumination, an upper bound of 13 mm for the device diameter was chosen. To balance the needs for visualization and the manipulation of tissue while minimizing the angle of view of the scanning system, we chose a standoff distance of 20 mm. Lastly, we chose a target spot size of 250 lam and a target surface speed of 100 mm/s, both in accordance with the scanning systems used in TLM.

Many different lasers are used in laryngeal surgery, including $CO_2$, potassium titanyl phosphate (KTP), and diode lasers. While $CO_2$ lasers are the preferred choice in many contexts, optical fibers transmitting this wavelength at high power tend to have a large core diameter, which implies a spot size that would exceed our design requirements. We, therefore, designed an exemplification of the device to be used with a diode laser that can be transmitted at high power (60 W) through a 35-μm core PM780-HP fiber from Nufern Inc. For this prototype, however, we validated its mechanics with a low-power fiber-optic inspection laser. We chose a 6.17-mm-focal-length collimator and a 38.1-mm focusing lens, which should yield a 210-μm spot diameter when combined with an optical fiber of 35-μm core diameter and a numerical aperture of 0.12. Both lenses were aspherical plano-convex to reduce aberrations. We chose mirror sizes of 2×2 mm and 2×5 mm with 40° initial angles, which were chosen in accordance with the kinematic analysis described, below. We chose to use an off-the-shelf factory-aligned fiber-coupled collimator (Thorlabs' F110 FC-633) to simplify integration at the expense of increasing device size.

Actuator lengths of 10.6 mm and 12.1 mm were chosen in order to achieve suitable displacement while not greatly lengthening the device. We assumed that the transmission stiffnesses would be approximately equal to the output stiffness of the actuators, implying a factor of two decrease in actuator deflection in situ versus free deflection. Under this assumption, the deflections of the actuators at 200 V (the upper limit on operating voltage to avoid damage to the piezoceramic actuator materials) are ±200 μm and ±220 μm, respectively.

Figure 12:
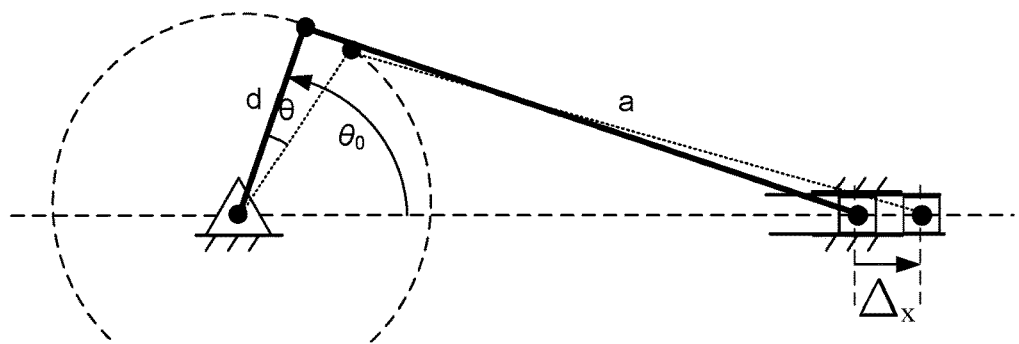
FIG. 12 shows the crank-slider transmission motion schematically represented with chosen design values shown in the table.
Figure 13:
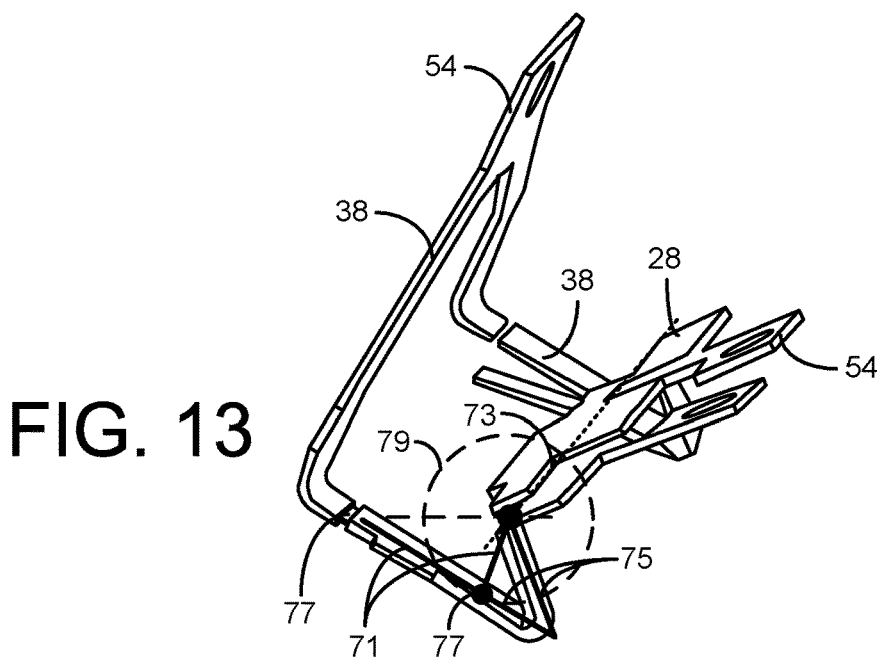
FIGS. 13 and 14 include depictions of the crank-slider arms on the fabricated linkages of the first instantiation of the end effector, where
Figure 14:
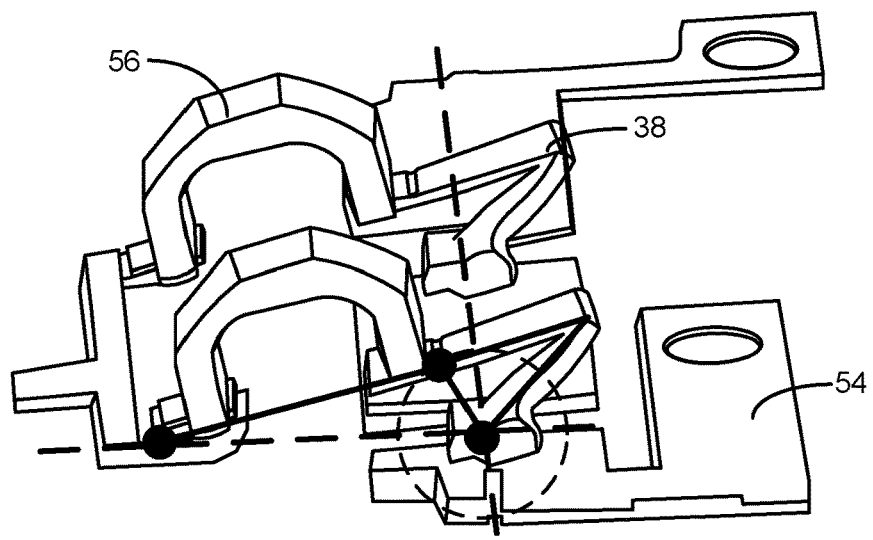

Using the optical model, described above, and considering placement of the mirrors to minimize device diameter, we determined that advantageous ranges of motion were ±10° for the first mirror and ±15° for the second mirror. To generate these motions, the crank slider link lengths [where link (a) has a 2-mm length for both mirrors and wherein the length of link (d) is 0.9 mm for the first mirror and 0.6 mm for the second mirror) shown in FIG. 12 were chosen in accordance with the crank-slider relation:

$$\theta = \cos^{-1}\left(\frac{d^2 - a^2 + x^2}{2dx}\right) - \theta_0, \quad (1)$$

$$x = x_0 + \Delta_x$$

where $\theta_0$ is the initial angle of the crank slider, $\Delta_x$ is the actuator deflection, and $x_o$ is the initial distance between the slider and the pivot. The initial angle, $\theta_0$, is 70° for the first mirror and is 75° for the second mirror. Of the two links, the length of the crank arm affects the output motion the most—the smaller it is, the larger the output movement and, therefore, the higher the transmission ratio. Also of note is the initial angle of the mechanism, which trades off symmetry for output amplitude. We chose the linkage configuration that achieved the desired range of motion while minimizing asymmetry. The fabricated linkages are shown in FIGS. 13 and 14.

Figure 15:
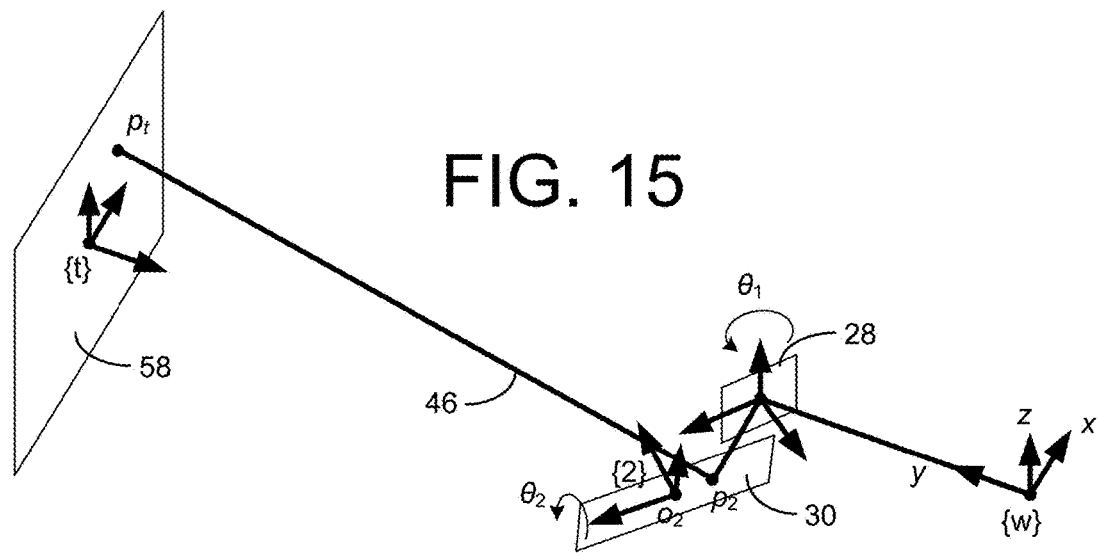
FIG. 15 is a diagrammatic representation of a laser-scanning system with key symbols defined.
Figure 16:
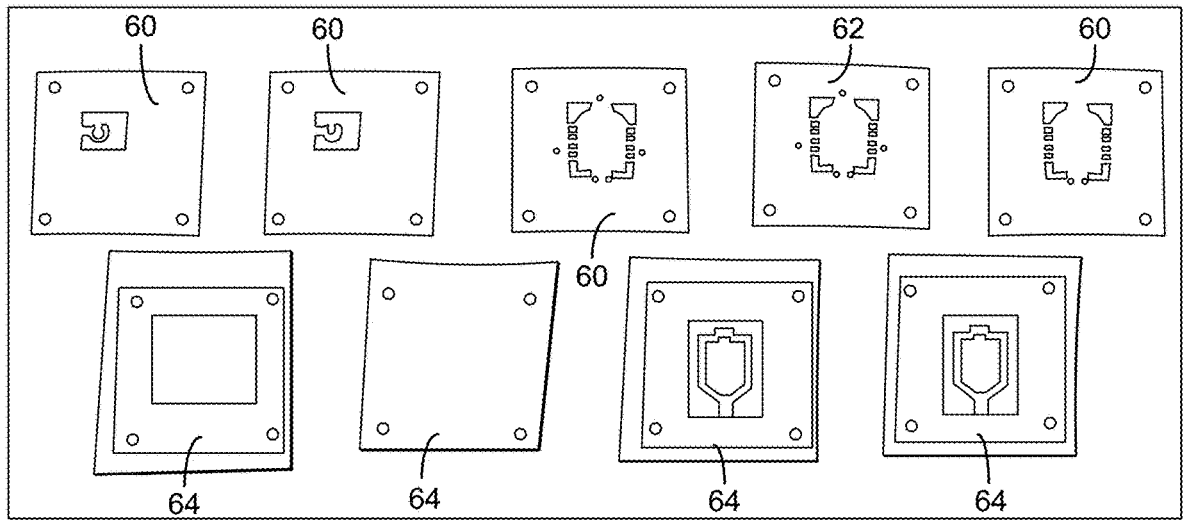
FIGS. 16-21 show a linkage manufacturing process.

Given the mirror angles determined by the crank-slider relation, expressed in Equation 1, the laser-spot location on the target plane can be found using the vector formulation of specular reflection. Symbols and geometric definitions used are given with the system schematic shown in FIG. 15, which shows the trajectory of a laser beam 46 reflecting off of the first mirror 28 and second mirror 30 to the target plane 58. The $j^{th}$ basis vector of the $i^{th}$ coordinate system is represented by $e_j^i \in R^3$. The unit vector directed from point, $p_j$, to point, $p_k$, with respect to the $i^{th}$ frame is represented by $\hat{v}_{jk}^i \in R^3$. The orientation of the $j^{th}$ coordinate system with respect to the $i^{th}$ coordinate system. Elementary rotation about the i axis by angle, θ. $H_y$ is the Householder transformation about the y-axis.

The orientations of the mirrors in 3D space are given by the following equations:

$$R_1^w = R_{z,\theta_{1,0}} R_{z,\theta_1}, \text{ and} \quad (2)$$

$$R_2^w = R_{z,(\theta_{1,0}-\pi)} R_{y,-\pi/2} R_{z,\theta_2}, \quad (3)$$

where $\theta_{1,0}$ is the design variable denoting the initial orientation of the first mirror. Now, the beam 46 reflected from the first mirror 28 has the following direction, $\hat{v}_{12}^1$:

$$\hat{v}_{12}^1 = H_y(R_1^w)^{-1} e_2^2, \quad (4)$$

The beam 46 then intersects the second mirror 30 after a distance, $d_{12}$, expressed as follows:

$$d_{12} = (\sigma_2 - \sigma_1)^T e_2^2 / (R_1^w \hat{v}_{12}^1)^T e_2^2. \quad (5)$$

Thus, the location, $p_2$, of the laser beam 46 on the second mirror 30 is given by the following equation:

$$p_2 = \begin{bmatrix} R_1^w & p_1 \\ 0 & 1 \end{bmatrix} \begin{bmatrix} d_{12}\hat{v}_{12}^1 \\ 1 \end{bmatrix}. \quad (6)$$

Similarly, the reflected beam 46 from the second mirror 30 has the direction, $\hat{v}_{2t}^2$:

$$\hat{v}_{2t}^2 = H_y(R_2^w)^{-1} R_1^w \hat{v}_{12}^1, \quad (7)$$

and intersects the target plane 58 after a distance, $d_{2t}$:

$$d_{2t} = (o_1 - o_2)^T e_3^t / (R_2^w \hat{v}_{2t}^2)^T e_3^t. \quad (8)$$

Finally, $p_t$, the location of the laser spot on the target plane is given by the following equation:

$$p_t = \begin{bmatrix} R_2^w & p_2 \\ 0 & 1 \end{bmatrix} \begin{bmatrix} d_{2t}\hat{v}_{2t}^2 \\ 1 \end{bmatrix}. \quad (9)$$

Figure 17:
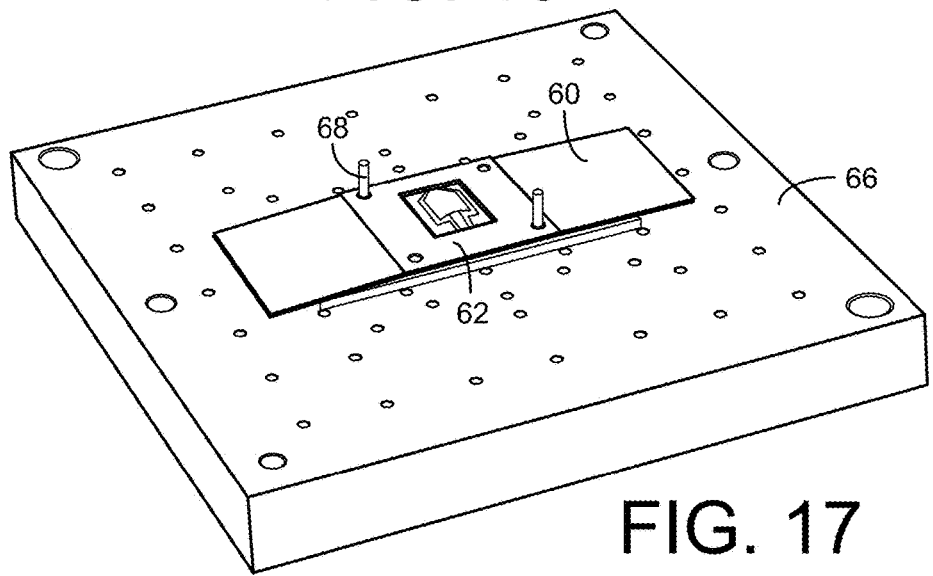
Figure 18:
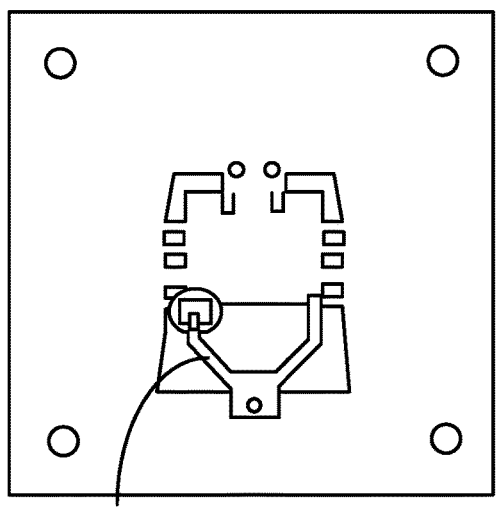
Figure 19:
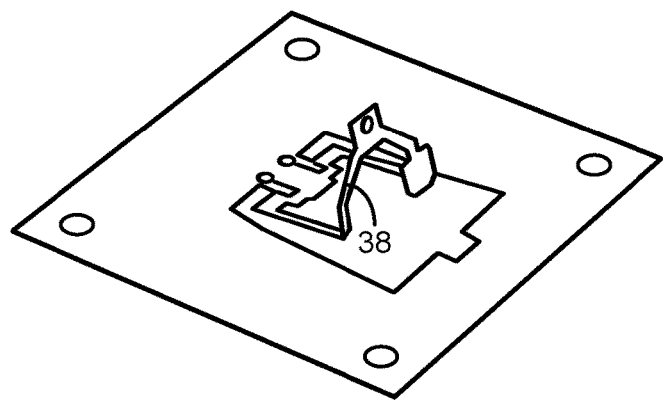
Figure 20:
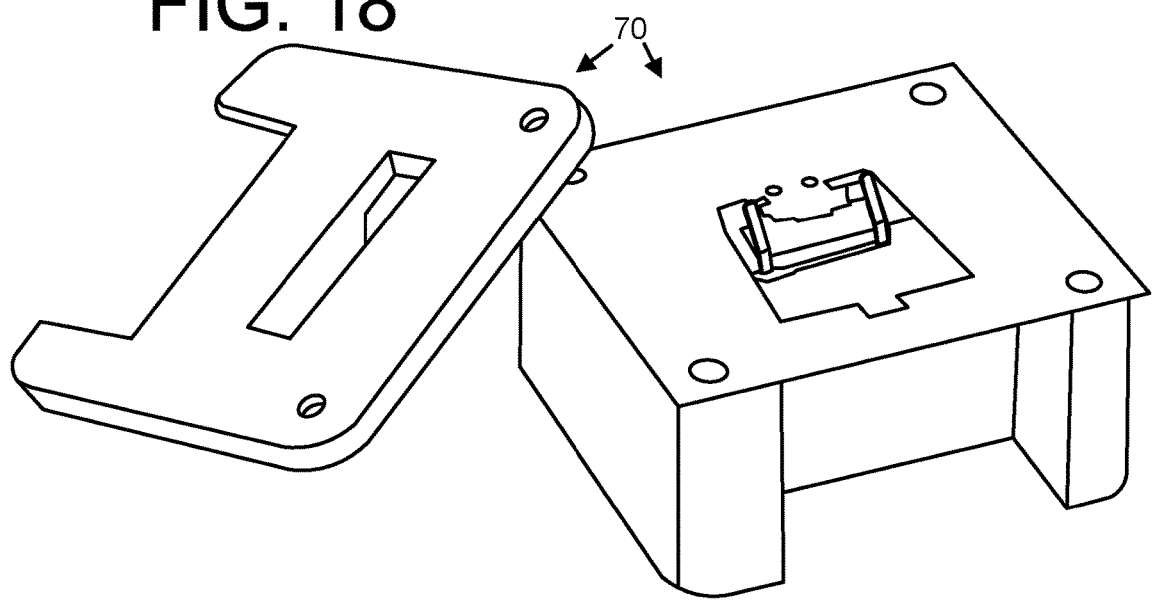
Figure 21:
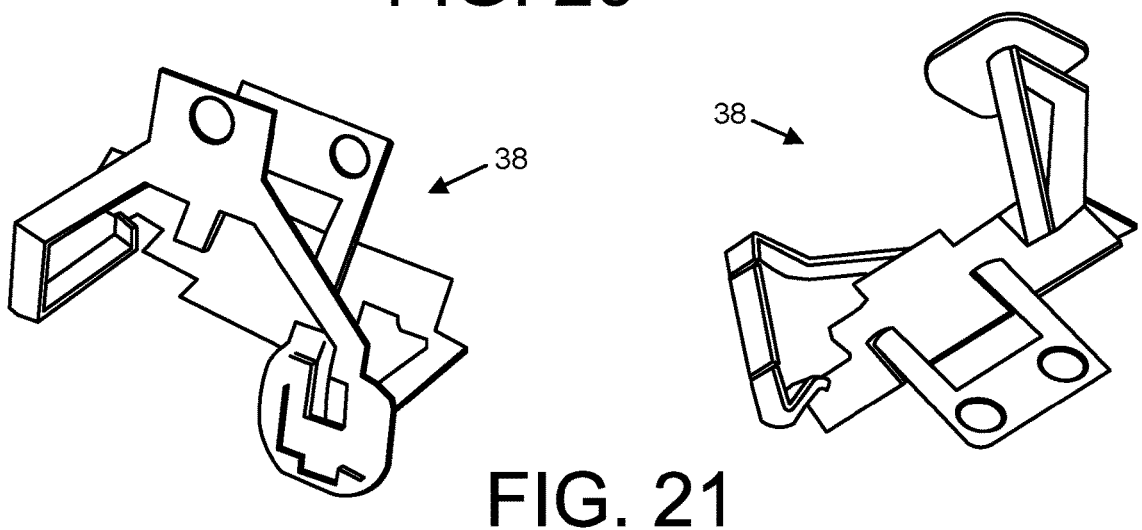

The manufacturing process used for fabricating the transmission linkages is based on the approach developed in P. S. Sreetharan, et al., "Monolithic fabrication of millimeter-scale machines," Journal of Micromechanics and Microengineering, Vol. 22, No. 5, 055027 (2012)] and is shown in FIGS. 16-21. Individual layers of a rigid material 60 (e.g., steel), a more-flexible material 62 (e.g., polyimide), and adhesive 64 (e.g., acrylic adhesive) were cut using a 7-W, 355-nm DPSS laser micromachining system (Oxford Lasers E Series) before being aligned and set into a heated press (the lower plate 66 of which is shown in FIG. 17) to bond the layers 60, 62, and 64 together. The bonded laminate is removed from the press, and preliminary release cuts are made, as shown in FIG. 18. The laminates are then bent into their desired configurations, as shown in FIG. 19; the first mirror transmission involves the use of an assembly jig 70, as shown in FIG. 20, to bend it to the correct angles, while the second mirror makes use of the alignment pins used for stacking. The laminates are then locked in their aligned configuration using cyanoacrylate (CA) glue, before performing final cuts to release the desired degrees of freedom. Each linkage 38 is set under a confocal microscope, and its functional dimensions are measured to validate the process. The manufacturing of the linkages 38 is a very repeatable process, with a standard deviation less than 4% of the desired value in all twelve linkages built, which corresponds to a 5% variation in the linkage transmission ratio. The laminate transmission linkage 38 will bend (approximating a pivot) at the longitudinal gaps between the rigid links wherein the flexible material is exposed.

The small link lengths of the crank sliders make their assembly challenging, but by bending their physical arms backwards to create virtual links (as seen in FIGS. 13 and 14), their handling is made significantly easier. Moreover, by using this approach, the flexures' bending angles are zero at rest, which makes it easier to ensure they stay inside the elastic regime of deformation.

The linkages' ground connections were attached to a 7075 aluminum alloy base structure manufactured using a five-axis CNC machine (Bridgeport, Hardinge, Inc.). The mirrors were made by laser cutting an aluminum-sputtered 100-μm-thick fused-silica wafer (from Denton Vacuum Desktop Pro). A protective gel layer was added on the mirror to protect the reflective coating during the assembly. The linkages were then bonded to their respective actuators before being inserted into the mechanical structure and held in place with alignment pins and a press-fit plate. The actuator base and transmission ground linkages were then bonded to the mechanical structure with cyanoacrylate glue. Finally, fabrication was completed by carefully removing the protective gel layers from the mirrors.

Figure 22:
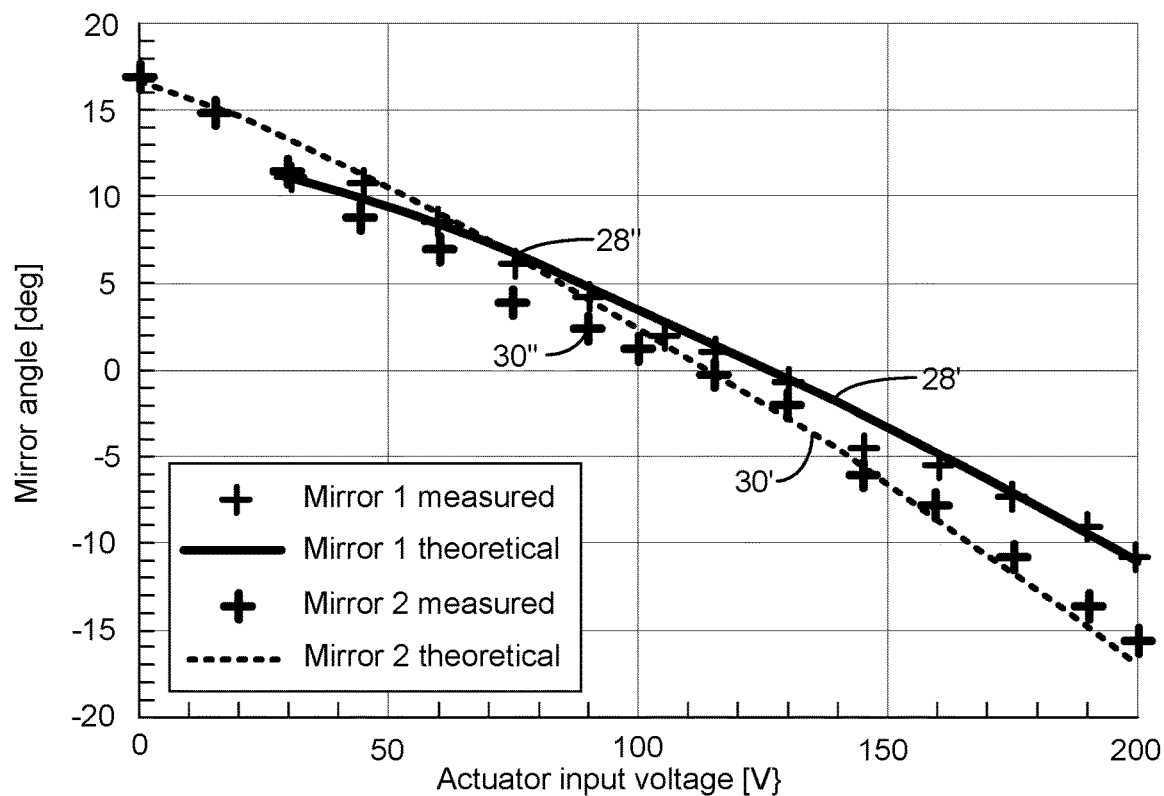
FIG. 22 plots the measurements of mirror angle as a function of actuator voltage for the first mirror 28" and for the second mirror 30" of the first instantiation of the end effector. The overall trend is captured well by the theoretical models for the first mirror 28' and the second mirror 30', with mean absolute errors of 0.6° and 1.2° for the first and second mirrors, respectively.

To validate the crank slider kinematic model (Equation 1), mirror angle and actuator displacement were measured as a function of actuator voltage. Mirror angle was measured under static voltage input using a high-zoom inspection camera (PIXELINK PL-B741F from Pixelink), and actuator displacement was measured under a 1-Hz quasi-static cyclic input using a laser Doppler vibrometer (a PSV-500 vibrometer from Polytec GMBH). In FIG. 22, measured 28"/30" and predicted 28'/30' mirror angles are plotted as a function of actuator inputs, with the theoretical values drawn from the measured actuator displacements at a given voltage. The results show that the model captures the broad behavior of the linkage well. The measured data have mean absolute errors of 0.6° and 1.2° for the first mirror 28" and second mirror 30", respectively.

Figure 23:
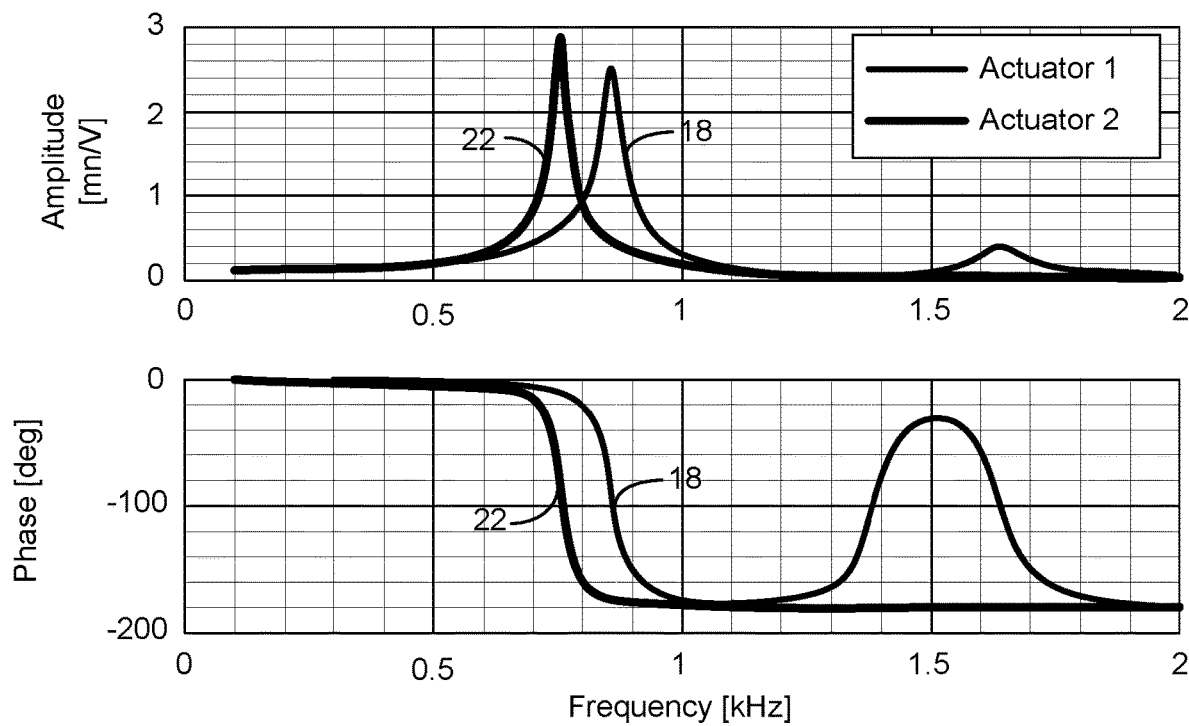
FIG. 23 plots the frequency response of the actuator-transmission-mirror subsystems for the first-linkage actuator 18 and for the second-linkage actuator 22 of the first instantiation of the end effector.

In order to find safe bounds on input drive frequency, we conducted frequency analyses on both motion actuator-transmission-mirror subsystems. Data were collected under low-voltage, white-noise input using the same laser Doppler vibrometer. The results are shown in FIG. 23; as expected, both subsystems closely resemble second-order linear systems. The resonant frequencies of 850 Hz and 750 Hz accord with physical intuition—the free-beam resonance of the actuators (1.6 kHz) has been reduced due to the added mass of the transmission.

Figure 24:
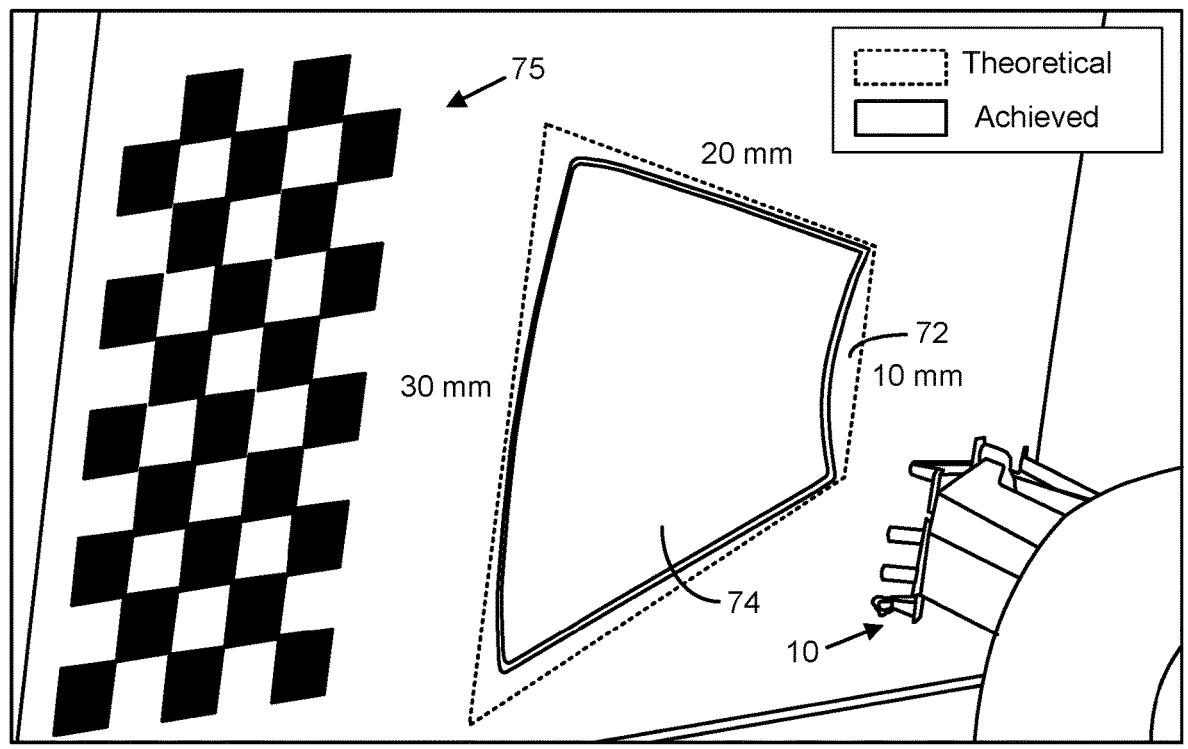
FIG. 24 shows a laser-spot-position tracking setup for the first instantiation of the end effector, as viewed from a high-speed camera. The theoretical field of view 72 and the achieved field of view 74 from a 20-mm standoff distance are shown.

To validate the beam-steering capabilities of the device, we created a benchtop scanning arena incorporating a calibrated high-speed camera (a PHANTOM V710 camera from Vision Research, Inc.) with a 200-mm macro lens and two non-flicker flood lights, all mounted on an optical table. The camera view is shown in FIG. 24 along with the grid 75 used for image registration. One pixel corresponds to 50 μm in the image plane. We fixed our device on the optical table at our determined stand-off distance of 20 mm from the target.

We then calibrated the scanner by sweeping the voltage space and tracking the laser-spot position. The overall achieved field of view 74 matches the model prediction 72 well, as shown in FIG. 24. However, unmodeled compliance in the system and assembly misalignment created a slight warping of the laser task space. Rather than adding extra degrees of freedom to our model and calibrating it, we chose to use a lookup-table approach for controlling the laser-spot position.

Figure 25:
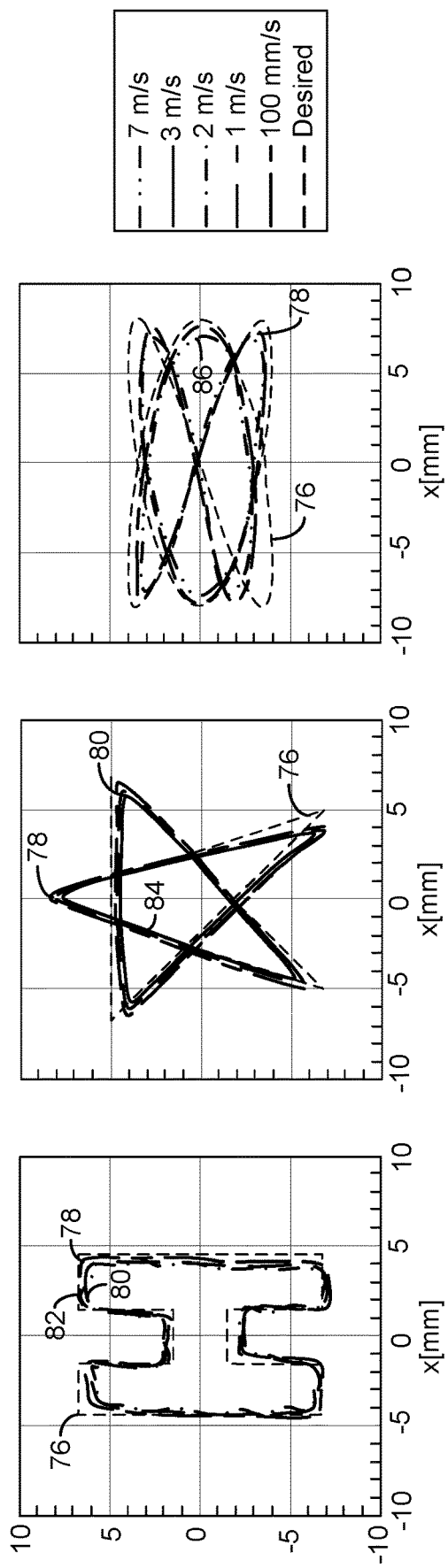
FIG. 25 shows shapes drawn at different speeds using the first instantiation of the end effector, demonstrating the open-loop trajectory-following capabilities of the laser scanner. The high-speed performance of the system is shown through its repeatability across a range of commanded velocities.

This approach yields reasonable results for task-space-trajectory following, as shown in FIG. 25, where the desired trajectory is shown with plot 76. Three shapes, an "H" (at left), a "star" (at center), and a Lissajous figure (at right), were drawn across a range of speeds (at 100 mm/s, shown via plot 78; at 1 m/s, shown via plot 80; at 2 m/s, shown via plot 82; and at 3 m/s, shown via plot 84; and at 7 m/s, shown via plot 86). Each shape is shown at a base speed of 100 mm/s 78 and at the highest speed that it could be reproduced before oscillations in the transmissions erode the device's tracking performance. Such oscillations just emerge as visible at 2 m/s (plot 82) in the "H" trajectory. Of the three shapes, the "H" is the most challenging due to the rapid, abrupt changes in the trajectory. The Lissajous figure is simplest, because the drive voltages on the actuators are smooth and nearly sinusoidal and, thus, suffer little loss in performance up to 7 m/s (plot 86).

The prototype device satisfies the majority of the design requirements: field of view (slightly less than 10×20 mm), scanning speed (up to 7 m/s), and scanning device size (11 mm). A combination of assembly misalignments and unmodeled off-axis compliance led to some error in our model for laser-spot position, as shown by the warping of the achieved field of view in FIG. 24. This can be improved by minimizing the amount of manual manipulation needed for assembly and by using other flexure materials or geometries with more suitable compliance ratios.

While calibration and feedforward control allow for qualitative trajectory following, sizeable deviations from the desired trajectories remain, likely because the calibration was conducted statically and doesn't capture dynamic, non-linear, or hysteretic effects. Thus, feedback control may be necessary for accurate control of the laser-spot position. To that end, embodiments of the device may incorporate angle sensing on the mirror output or means to feed back the laser position directly to the controller.

Another important next step is the integration of high-powered optics. To that end, higher-quality mirror coatings can be incorporated. Of available mirror coatings, gold is an advantageous option, as it is highly reflective (>97%) at advantageous wavelengths of 800 to 1000 nm. Dielectric coatings can also be considered, as they can reach up to 99.8% reflectivity, but they are much more selective to wavelength.

The somewhat fragile mechanical structure of the mirrors and linkages can be enclosed to protect them, and the mirrors can be protected from fluid flow at the surgical site. This device can be used alongside existing transoral robotic tools for visualization and tissue retraction, so tasks can be coordinated with these tools.

In various exemplifications, a gradient-index collimating lens collects light from a ferrule-terminated optical fiber and directs it into a miniature plano-convex focusing lens. The light is reflected by a 45° angle-of-incidence mirror and into a miniature two-mirror galvanometer. Flexible linkages convert the quasi-linear motion of piezoelectric bending actuators into the rotational motions of the galvanometer mirrors. A cylindrical profile facilitates integration with existing surgical tools.

Below, we describe the design, fabrication, and control insights that culminate in our laser-steering solution. We first describe general design considerations for miniaturizing the galvanometer portion of the device. This is the least straightforward component to miniaturize both in terms of design and fabrication. Next, we present details for the design and construction of each component and the assembly thereof. Third, we report the methods used for static position control and characterization. Last, we describe the dynamic properties of the device, demonstrate the ability for high-bandwidth operation, and interface the device with a commercial colonoscope.

Figure 27:
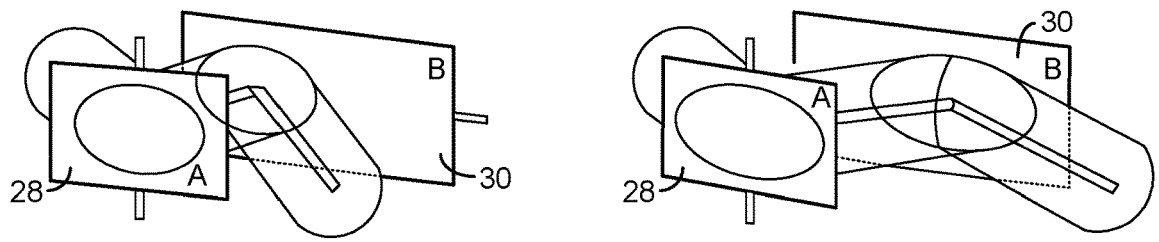
FIG. 27 shows two mirror-angle configurations for a two-mirror galvanometer.
Figure 28:
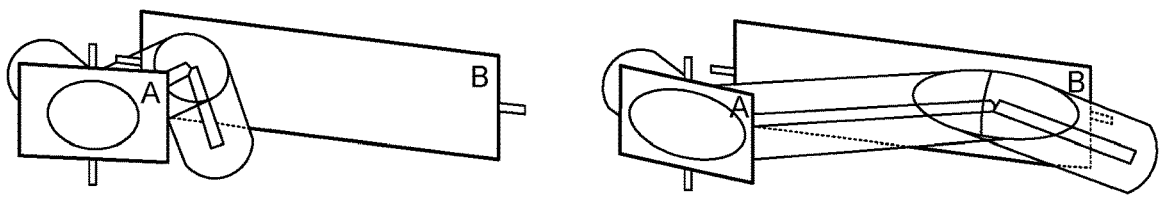
FIG. 28 shows two additional mirror-angle configurations for a two-mirror galvanometer.

The galvanometer is the most complex component of the device to design for miniaturization, but there are some general insights on the design space that guide our efforts. The objective is to minimize the distance between the mirrors, given the beam size, mirror size, and desired range of motion, all while avoiding collisions between the mirrors and between the reflected beam and previous mirrors in the optical path (see FIGS. 26-28). An important high-level design consideration is the number of mirrors used. Somewhat counter-intuitively, a three-mirror design can actually be made smaller than a two-mirror design, if the same range of motion is desired for each.

Figure 26:
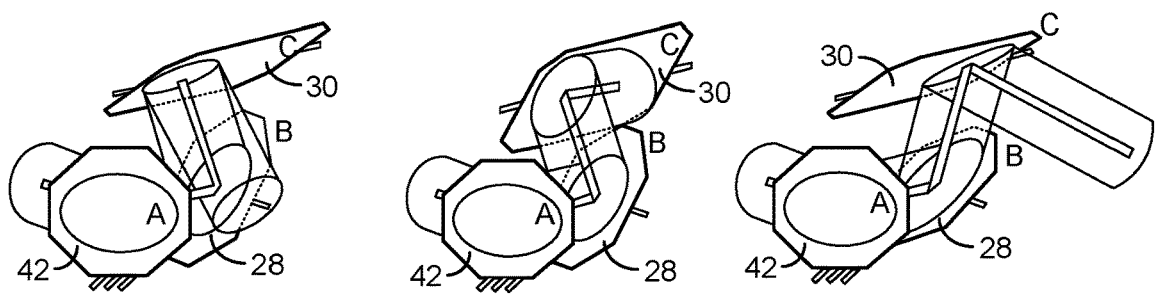
FIG. 26 shows three mirror-angle configurations for a three-mirror galvanometer.

First, consider the three-mirror design shown in three configurations FIG. 26, where the incident beam enters from the left before being reflected, in turn, by the fixed mirror 42, the first active mirror 28, and the second active mirror 30 (with a circumscribed diameter of 4 mm). In the image at left, first and second active mirrors 28 and 30 are rotated at +10°. In the image at center, the first active mirror 28 is rotated at +10°, while the second active mirror 30 is rotated at −10°. In the image at right, the first active mirror 28 is rotated at −10°, while the second active mirror 30 is rotated at +10°. If the distance between the fixed mirror 42 and the first active mirror 28 is too small, then the reflected beam from the second active mirror 30 will intersect the fixed mirror 42. If the distance between the first active mirror 28 and the second active mirror 30 is too small, then those mirrors will collide. However, increasing the distance between mirrors not only increases device size, but it also means that larger area mirrors are needed to collect the reflected light for the same range of motion. The illustrated three-mirror design balances all of these considerations to yield a device with +/−10° range of motion on each active mirror in a 4-mm diameter footprint. Note that the use of chamfered corners on the mirrors increases the range of motion by preventing collisions in critical locations.

The first two-mirror design (shown in two configurations in FIG. 27) has the same diameteral footprint as the three-mirror design but its range of motion is halved on the first mirror axis. In the image at left, the first active mirror 28 is rotated at a +5° angle, while the second active mirror 30, which has a circumscribed diameter of 4 mm, is at a neutral, 0°, angle. In the image at right, the first active mirror 28 is rotated at −5°, while the second active mirror 30 is at a neutral, 0°, angle. An insidious set of trade-offs leads to this result; if the mirrors 28 and 30 (both active) are too close together, then the beam reflected from the second active mirror 30 will intersect the first active mirror 28 for large positive rotation angles of the first mirror 28. On the other hand, if the distance between the two mirrors 28 and 30 is increased, then the second mirror 30 must be enlarged to accept the incident light for large negative rotation angles of the first mirror 28. This is the second two-mirror design (FIG. 28); it achieves the same range of motion as the three-mirror design at the expense of a 50% increase in diameter (the circumscribed diameter of the second mirror 30 is 6 mm). In the image at left, the first active mirror 28 is rotated +10°, while the second active mirror 30 is at a neutral, 0°, angle. In the image at right, the first active mirror 28 is rotated −10°, while the second active mirror 30 is rotated +8°.

Accordingly, the three-mirror galvanometer (FIG. 26) achieves a larger range of motion than a two-mirror design of the same size (FIG. 27), and a 50% larger diameter two-mirror design (FIG. 28) is needed to achieve the same range of motion as the three-mirror design. Range of motion is primarily determined by the ability of the mirrors to fully capture and reflect the incident light, but it is limited by the need to avoid collisions between mirrors and collisions between the reflected laser and previous mirrors in the optical path. These sample configurations show the limits of the range of motion at which these collisions are about to occur.

Throughout this analysis, we assumed a fixed beam diameter of 1 mm, which is somewhat larger than the low-power pointing laser used herein for device validation, but it is a reasonable upper bound for a collimated high-power beam. For simplicity, we also chose the neutral position of each mirror to be at a 45° angle of incidence with the incoming beam, allowing this to slightly deviate from 45° might yield slightly different results but would not change the structure of the design trade-offs. We also assumed that a symmetric range of motion is desired. Once again, if this was not the case, then the resulting design might change slightly, but the nature of the design space need not change. Lastly, it should be emphasized that we have been considering the case of the exiting ray being parallel to the incoming fiber (forward looking). If we wanted the exiting ray to be perpendicular to the incoming fiber (side looking), there would be no reason to use a three-mirror design; a two-mirror design would be perfectly acceptable in terms of miniaturization and range of motion. However, because most energy delivery tools used in surgery are forward-looking, we chose to use that configuration for these exemplifications of our device, though other exemplifications of the device can readily be employed in side-looking device.

Figure 29:
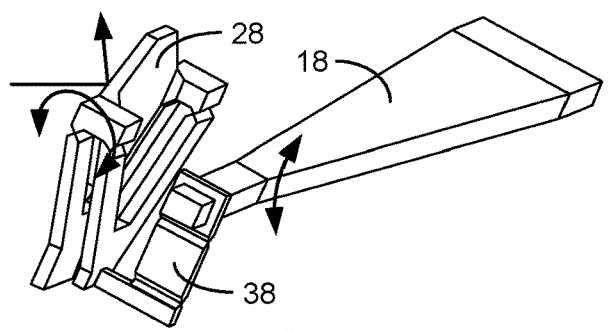
FIG. 29 shows the first active mirror 28 with its associated actuator 18 and passive transmission linkage 38 of the second instantiation of the end effector.
Figure 30:
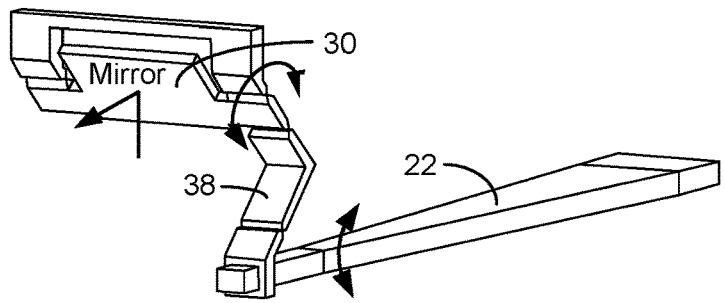
FIG. 30 shows the second active mirror 30 with its associated actuator 22 and passive transmission linkage 38 of the second instantiation of the end effector.

With those general insights in hand, we undertake the detailed design and fabrication of the device. For construction, we use a mixture of off-the-shelf components and custom-made parts that are primarily created using laser micromachining (using an Oxford Lasers E Series with Coherent Avia 355-7 laser and a Canon galvanometer). The kinematic structures of the piezoelectric bending actuator motion-transmission assemblies of a three-mirror galvanometer are shown in FIGS. 29 and 30, including the bending actuators 18 and 22, transmission linkages 38, and mirrors 28 and 30. The assemblies convert the quasi-linear (parabolic) input motion into rotational motion of the mirrors.

Figure 31:
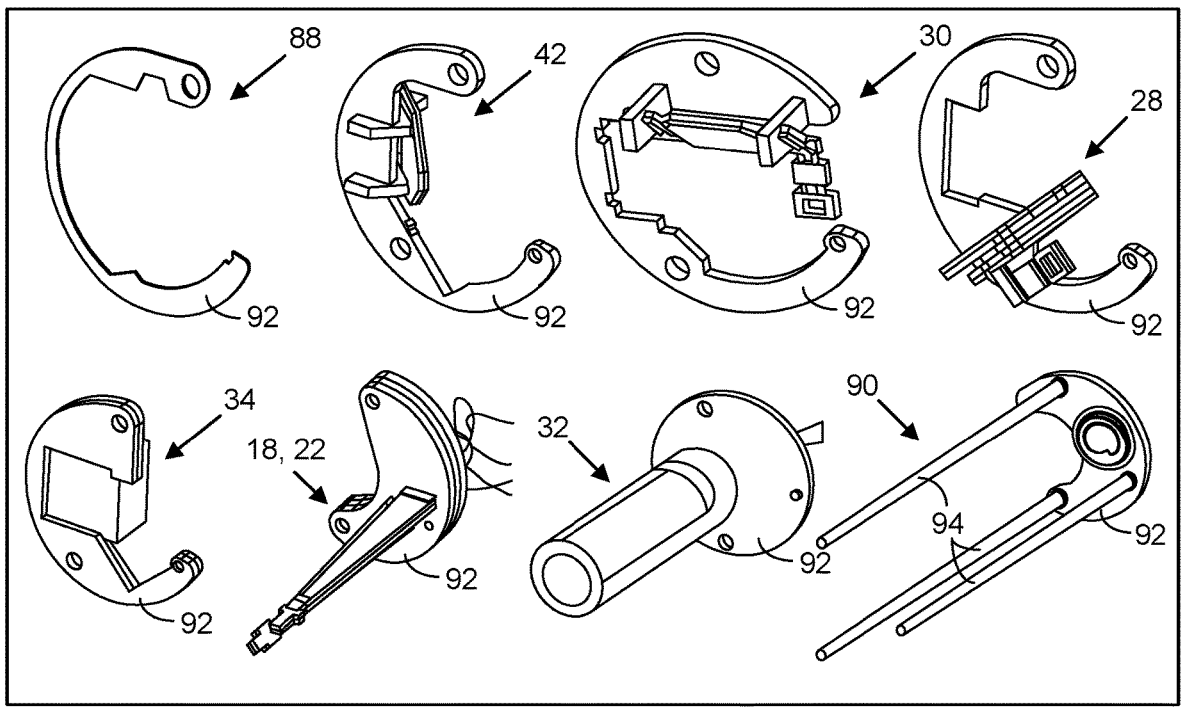
FIG. 31 shows modular components of the second instantiation of the laser-steering end effector.

The components of the three-mirror galvanometer before assembly are shown in FIG. 31 (in order of assembly—first row left to right, followed by second row left to right). The illustrated components include a retaining clip 88, a fixed mirror 42 assembly, a second active mirror (y-axis) 30 assembly, a first active mirror (x-axis) 28 assembly, a focusing lens 34 assembly, a piezoelectric actuator 18 and 22 assembly, a collimating lens 32 assembly, and a support superstructure 90. The retaining clip; mirrors 42, 28, and 30; lenses 34 and 32; and actuators 18 and 22 are each mounted on disk platforms 92 with orifices through which the platforms 92 are slidably mounted onto rods 94 of the support superstructure 90, thereby providing a detachable, modular structure. These components can be formed via cutting with a UV laser. The active mirror 28 and 30 assemblies and piezoelectric actuator 18 and 22 assemblies can also involve precision lamination. Sputter deposition can be used in forming the mirror 28, 30, and 42 assemblies. The lenses can 32 and 34 be off-the-shelf components. Finally, diamond grinding can be employed in shaping the focusing lens 34.

Specific details for component design, fabrication, and function are as outlined, below.

Steel-rod superstructure 90: This component consists of two 500 μm and one 300 μm-diameter stainless-steel rods 94 (Misumi USA) onto which the remaining components are assembled. The rods 94 are orthogonally located into a FR4 disk 92 using an alignment jig. A spring steel preload spring to compress and hold the assembled components in place is attached to the disk 92. All components were laser micromachined.

Ferruled fiber and collimating lens 32: An off-the-shelf ferrule terminated optical fiber (SMPF0106-FC, Thor Labs) was assembled with a gradient index collimator 32 (GRIN2306A, Thor Labs) and attached to an FR4 support disk 92.

Piezoelectric bending actuators 18 and 22: The actuators 18 and 22 were made to size using the process and materials described in N. T. Jafferis, M. J. Smith, and R. J. Wood, "Design and manufacturing rules for maximizing the performance of polycrystalline piezoelectric bending actuators," Smart Materials and Structures, Vol. 24, No. 6, p. 065023 (2015). We chose actuator dimensions in accordance with the available space adjacent to the optical components: an active length of 7 mm, a tip length of 1.8 mm, a bridge length of 0.5 mm, a base width of 1.4 mm, and a tip width of 0.4 mm.

The actuators are driven in the biased unipolar configuration with a fixed bias voltage, so each is controlled by a single time-varying input signal ranging from zero to the bias voltage. To achieve a sizeable output displacement while ensuring that the tensile strain in the piezoceramic is well below the failure limit, we chose a fixed bias voltage of 200 V. Under these drive conditions, the actuators achieve free displacement of +/−200 μm and have a first resonant frequency of 2.6 kHz.

Focusing lens 34: The focusing lens 34 was acquired as an off-the-shelf component (#89-003, Edmund Optics) and ground down to size using an alignment jig and a diamond cut-off wheel. Registration marks laser pre-engraved into the lens 34 allow alignment of the optical center after grinding.

Articulable mirrors 28 and 30 and motion transmissions: These are complex assemblies of rigid and flexible components fabricated using lamination techniques. They can include four-bar crank-slider linkages formed from stainless steel, polyimide, and a heat-curable acrylic adhesive (PYRALUX adhesive from Dupont Inc). The mirrors 28 and 30 are located on the cranks, and the sliders each interface with one of the piezoceramic actuators 18/22. The x-axis (first) transmission additionally contains a linearizing linkage to compensate for the out-of-plane motion of the bending actuator tip. These are shown schematically in FIGS. 29 and 30. The mirrors 28 and 30 are made from sputtered aluminum (Denton Desktop Pro PVD system, Denton Vacuum LLC, Moorestown, NJ, USA) on a 100-μm fused silica substrate and singulated using a UV laser.

The detailed design of the transmissions follows from the actuator properties. We wanted to achieve +/−10° of motion for each mirror (driven by bending of the actuator in either direction) in line with the state-of-the-art devices. To achieve this motion, there are two important design considerations: (1) the transmission ratios of the linkages and (2) the stiffnesses of the linkages relative to that of the actuators. Based on experience sizing similar mechanical components, we chose a target transmission ratio of 0.1°/μm and a target stiffness equal to that of the actuators. In the device, we achieved transmission ratios of 0.13°/μm and 0.12°/μm (due to small fabrication errors) and stiffnesses of 60% and 90% of the actuator stiffness.

Note that the stiffness of the transmission is parallel to the actuator stiffness and results in reduction of the free displacement of the actuators. Thus fabricated, we achieve ranges of motion of −12.5 to 20° and −11.2 to 13.7° for the two mirrors, respectively. The asymmetry corresponds to a small assembly misalignment and slightly nonlinear transmission kinematics. The neutral (zero) mirror angles and actuator positions correspond to the configuration for which the output beam is aligned along the longitudinal axis of the device.

Fixed mirror 42: This aluminum-sputtered fused silica mirror 42 is fixed at 45° relative to the incident light using two alignment blocks that, in turn, interface with an FR4 support disk 92.

Retaining clip 88: This spring-steel component fits onto grooves rastered into the stainless-steel rods 94 of the superstructure 90. It axially constrains the assembly in conjunction with the preload spring located on the superstructure base.

Spacer tubes and disks: The pieces are laser micromachined to ensure proper spacing and alignment between components. Their length (or thickness) are their critical dimensions.

We began characterizing the position control of the end effector by measuring open-loop repeatability, which is an important metric because it describes the fundamental limitations of the device physics to reproduce identical motions. Stiction, plasticity, and other phenomenon mean that identical inputs do not produce identical outputs. Unidirectional repeatability is a measure of repeatability in which measurement points are only approached from one direction. The maximum 2σ standard distance of the sampled points was 200 μm, which means that there is 95% confidence that any series of identical movements will fall within a 200-μm radius of dispersion about the mean trajectory.

The presence of hysteresis complicates position control. Hysteresis is a bi-directional effect that arises primarily from domain reorientation inside the piezoceramic actuator; it means that the laser position depends on the time history of the input. This dependence is clearly undesirable because it complicates control and makes use of the device unintuitive. To minimize the hysteretic effects, we implemented a feedforward compensation scheme. To validate our approach, we commanded star trajectories for uncompensated and compensated inputs. The raw inputs clearly show the effects of path dependence, while the corrected inputs show significantly improved tracking; this is, essentially, a measure of bi-directional repeatability. Quantitatively, we find that the maximum 2σ standard distance around the setpoints is 2.14 mm without compensation and 0.72 mm with compensation, which represents a reasonable improvement for feed-forward compensation; further improvement can be achieved with feedback control.

Because of the low dimensionality of the workspace and input space and because of the lack of sensor information, we chose to control the device using a direct model-free mapping between actuator input and laser-spot position, cascaded with the feed forward compensation for hysteresis. We fit third- and second-degree polynomial surfaces to the open-loop repeatability measurement data for the first and second mirrors, respectively. These fits were centered around 73 V and 93 V, respectively, which correspond to neutral angles of the mirrors.

Figure 32:
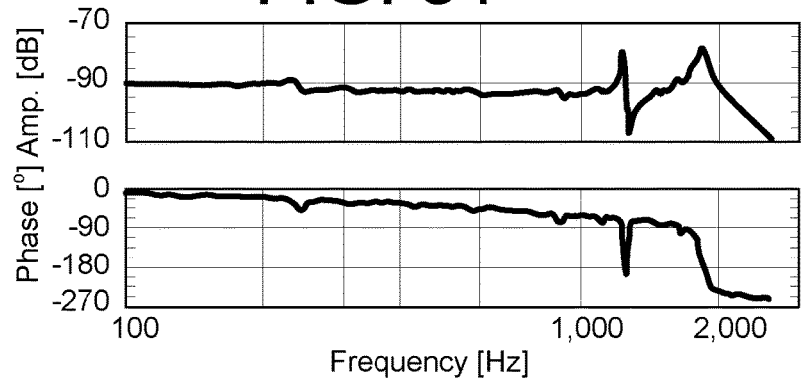
FIGS. 32 and 33 are plots of the frequency response of the first and second mirrors, respectively, of the second instantiation of the end effector in terms of phase and amplitude.
Figure 33:
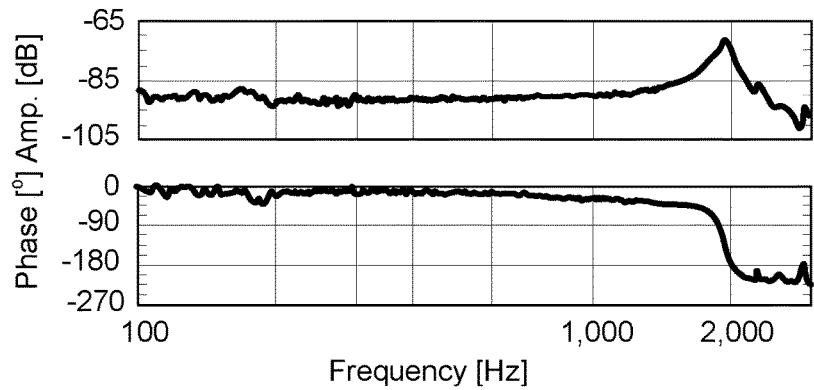

The system can be dynamically controlled and characterized. The bandwidth of the system is limited by resonant oscillation of the mirrors at high frequencies. The primary resonant frequencies for the two mirrors are 1.8 kHz and 1.9 kHz, as can be seen in the Bode plots shown in FIG. 32 (which plots the frequency response of the first active mirror to low-voltage white-noise input) and FIG. 33 (which plots the frequency response of the second active mirror). Additionally, there is a lower frequency mode at 1.2 kHz on the first mirror (likely due to twisting or another off-axis mode). To avoid exciting these modes, we use a finite jerk motion profiling scheme (also known as sigmoid or S profiling).

Figure 34:
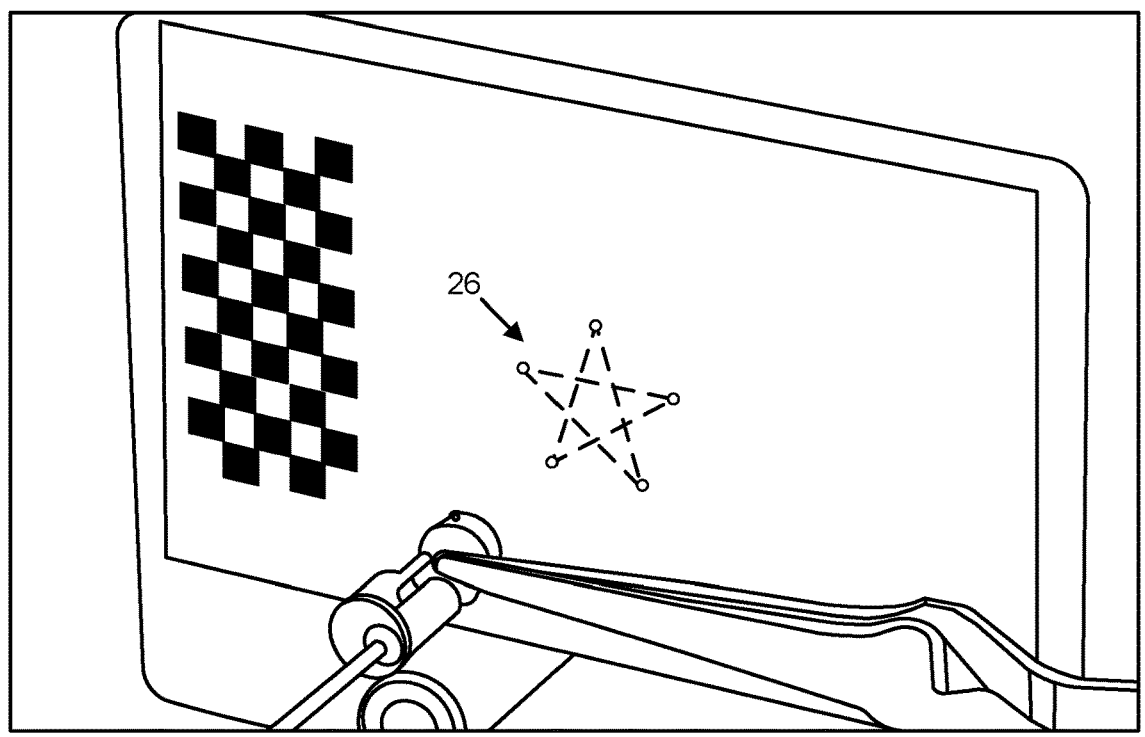
FIG. 34 is an image created by high-speed motion of the laser-steering system of the second instantiation of the end effector.
Figure 35:
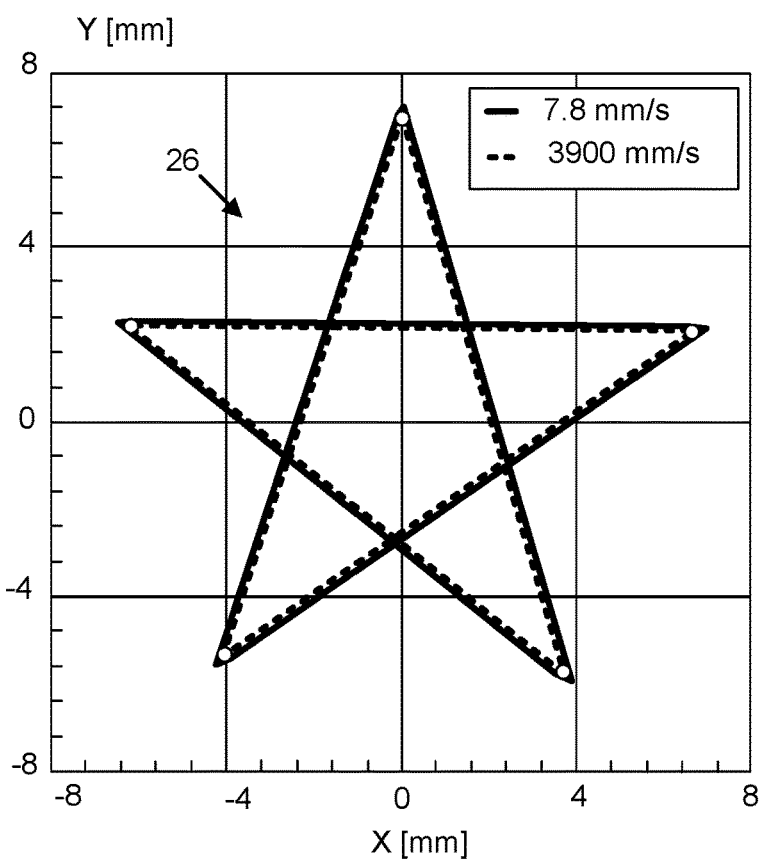
FIG. 35 shows how the high-speed image (generated at 3,900 mm/s) closely matches the trajectory generated by the laser system of the second instantiation of the end effector at a low speed (7.8 mm/s).

The system shows only minor deviation from static trajectories 26 at high speeds, as can be seen in FIGS. 34 and 35. There is only 5% deviation between the trajectories followed at low (7.8 mm/s—solid plot in FIG. 35) and high (3,900 mm/s—dashed plot in FIG. 35) speeds. Also, because of the two-axis control, the system can trace complex planar trajectories. The large bandwidth in the system can also be exploited to generate multi-modal profiles. These are trajectories in which a high frequency input is superimposed onto a low frequency one, which allows the user to change the effective area of energy application on the fly, which is particularly interesting for situations in which a large area needs to be controllably covered, as in large-area hemostasis.

Because of the low profile and small mass (e.g., 700 mg) of the laser-steering end effector, it can be readily interfaced with existing surgical tools. To demonstrate this, we attached it onto the end of a colonoscope (Olympus CF-100L) and performed a simulated polyp resection task on a benchtop surgical simulator. We demonstrate both teleoperated control using a standard input device (Phantom Omni) and robotic high-speed control of the laser along a registered incision trajectory.

This work points the way forward to new methods of controlling energy delivery in minimally invasive surgery. It can simultaneously address the following three important challenges in surgical technology: (1) giving surgeons greater control over the delivery of energy to soft tissue, (2) improving surgical instrument maneuverability and dexterity, and (3) reducing physical strain on both the operator and the materials. Our contribution herein, by giving surgeons control over the laser speed when interacting with tissue, enables the quality of laser/tissue interactions to be more widely tuned and optimized than is possible with existing statically wielded tools. Using the wristed articulation, surgeons will also gain access to previously unreachable lesions. Our design, fabrication, and modular assembly approach is an additional contribution that enables the creation of this device but will also be adaptable to other complex microrobotic systems and medical devices.

To achieve accuracy in line with the repeatability of the device, sensory feedback can be incorporated. A simple approach is to embed strain-gauge sensors within the piezoelectric bending actuators to estimate actuator position and to use current sensing to estimate actuator velocity. The mirror position can then be calculated from the transmission kinematics and the laser position estimated from a model of specular reflection. Measuring the mirror position directly would result in a better laser position estimate, but the pathway to a suitable miniature sensing method is not as straightforward as sensing the actuator motion. Alternatively, visual feedback could be used for high quality estimates, albeit perhaps at lower sample rates than is achievable with electromechanical sensors. In practice, some sensor fusion that blends these different pieces of information is likely the best approach.

Additionally, suitable high-power fibers, lenses, and mirrors can be incorporated in order to use the device with surgical lasers. The choice of components depends on the wavelength and power of the laser being used. For example, if a $CO_2$ surgical laser is being used, gold-sputtered aluminum mirrors and zinc-selenide lenses provide appropriate reflectance and transmission, respectively. Particular attention is paid to the "laser-induced damage threshold," which is a measure of the laser power that an optical component can experience before degradation.

Regardless of the laser modality used, the device can advantageously be encapsulated so as to be robust to the fluids and debris in the surgical environment and allow for sterilization. Because the tips of laser fibers can be damaged after extended use, incorporation of a method for decoupling the laser fiber from the device can be advantageous. This decoupling capability would allow the independent cleaning and cleaving of the laser fiber, which can significantly expand its lifetime.

Because the laser position is controlled electronically instead of through cable actuation, the energy control can be decoupled from the gross movement of the surgical tool on which it is deployed. This independence is especially important in flexible endoscopy, which often requires cumbersome manual motions including device handoffs, setting down the endoscope, moving one's hands multiple times to different parts of the instrument, and having another user operate the end effector. Accordingly, one can easily imagine how the use of a remote-control column, such as a joystick, that is not positionally dependent due to the spatial constraints of a cable and therefore can be mounted ergonomically somewhere on the endoscope or with a second operator away from the endoscope, would improve the efficient use of time in the operating room that is used for patient care and not for device handling.

Our laser steering approach also enables new approaches for endoscopic visualization and visual biopsy. In optical coherence tomography and confocal endomicroscopy, laser/tissue interactions are used to visualize sub-surface structures, and scanning allows a large area of tissue to be seen at once. Optical steering can also be used to increase the effective field of view of standard white light imaging tools, through stitching together a set of images acquired through rapid scanning. The scanning system and modular device assembly approach described herein can be adapted to the fabrication of millimeter-sized versions of those systems. Even smaller versions of these systems are built using laminate fabrication techniques that use electrostatic and electorothermal actuators to excite resonant scanning elements. Our approach presents advantages in terms of simplicity of construction and the ability to achieve a large quasi-static range of motion.

We also anticipate that this technology can be adapted for use in other microrobotic systems, particularly in micro aerial vehicles and satellites for which size and weight are at a premium. This technology enables the fabrication of miniature light detection and ranging (LIDAR) sensors used for mapping and navigation, as well as laser scanners used for wide-area atmospheric sensing of pollution.

In describing embodiments of the invention, specific terminology is used for the sake of clarity. For the purpose of description, specific terms are intended to at least include technical and functional equivalents that operate in a similar manner to accomplish a similar result. Additionally, in some instances where a particular embodiment of the invention includes a plurality of system elements or method steps, those elements or steps may be replaced with a single element or step. Likewise, a single element or step may be replaced with a plurality of elements or steps that serve the same purpose. Further, where parameters for various properties or other values are specified herein for embodiments of the invention, those parameters or values can be adjusted up or down by $1/100^{th}$, $1/50^{th}$, $1/20^{th}$, $1/10^{th}$, $1/5^{th}$, $1/3^{rd}$, $1/2$, $2/3^{rd}$, $3/4^{th}$, $4/5^{th}$, $9/10^{th}$, $19/20^{th}$, $49/50^{th}$, $99/100^{th}$, etc. (or up by a factor of 1, 2, 3, 4, 5, 6, 8, 10, 20, 50, 100, etc.), or by rounded-off approximations thereof or within a range of the specified parameter up to or down to any of the variations specified above (e.g., for a specified parameter of 100 and a variation of $1/100^{th}$, the value of the parameter may be in a range from 0.99 to 1.01), unless otherwise specified. Moreover, while this invention has been shown and described with references to particular embodiments thereof, those skilled in the art will understand that various substitutions and alterations in form and details may be made therein without departing from the scope of the invention. Further still, other aspects, functions, and advantages are also within the scope of the invention; and all embodiments of the invention need not necessarily achieve all of the advantages or possess all of the characteristics described above. Additionally, steps, elements and features discussed herein in connection with one embodiment can likewise be used in conjunction with other embodiments. The contents of references, including reference texts, journal articles, patents, patent applications, etc., cited throughout the text are hereby incorporated by reference in their entirety for all purposes; and all appropriate combinations of embodiments, features, characterizations, and methods from these references and the present disclosure may be included in embodiments of this invention. Still further, the components and steps identified in the Background section are integral to this disclosure and can be used in conjunction with or substituted for components and steps described elsewhere in the disclosure within the scope of the invention. In method claims (or where methods are elsewhere recited), where stages are recited in a particular order—with or without sequenced prefacing characters added for ease of reference—the stages are not to be interpreted as being temporally limited to the order in which they are recited unless otherwise specified or implied by the terms and phrasing.

What is claimed is:

1. A compact laser-steering end effector, comprising:
a frame with a proximal end and a distal end with a greatest dimension in a plane orthogonal to a longitudinal axis of no more than 13 mm;
at least two mirrors mounted proximate to the distal end of the frame, the mirrors including a first active mirror and a second active mirror;
a first actuator mounted to the frame and configured to change the tilt of the first active mirror relative to the frame; and
a second actuator mounted to the frame and configured to change the tilt of the second active mirror relative to the frame,
wherein a pathway is provided through the frame to deliver a laser beam to the mirrors, and wherein the mirrors are positioned and configurable via the actuators to reflect the laser beam off of each mirror en route to an external target.

2. The compact laser-steering end effector of claim 1, further comprising a third mirror positioned and configured to reflect the laser beam along with the first and second active mirrors.

3. The compact laser-steering end effector of claim 2, wherein the third mirror is fixedly mounted.

4. The compact laser-steering end effector of claim 1, wherein the first and second actuators are cantilevers.

5. The compact laser-steering end effector of claim 4, wherein the cantilevers are coupled with the mirrors via passive linkages configured to linearize out-of-plane motion of the cantilever.

6. The compact laser-steering end effector of claim 4, wherein the cantilevers are bimorph piezoelectric cantilevers.

7. The compact laser-steering end effector of claim 1, further comprising a surgical laser positioned to direct a laser beam through the compact laser-steering end effector to the mirrors for steering via reflection off the mirrors.

8. The compact laser-steering end effector of claim 7, further comprising a navigating laser positioned to direct a laser beam through the compact laser-steering end effector to the mirrors for steering via reflection off the mirrors.

9. The compact laser-steering end effector of claim 1, wherein the frame comprises a plurality of rods and a plurality of platforms mounted on the rods with components of the compact laser-steering end effector mounted on the platforms.

10. The compact laser-steering end effector of claim 1, wherein the compact laser-steering end effector extends from a microrobotic tool for energy delivery and to receive a laser beam input from an optical fiber extending through the microrobotic tool.

11. The compact laser-steering end effector of claim 10, wherein the pathway delivers the laser beam from the optical fiber to the mirrors.

12. The compact laser-steering end effector of claim 10, wherein the microrobotic tool is a minimally invasive surgical tool from which the compact laser-steering end effector extends.

13. A method for robotic laser steering, comprising:
generating a laser beam;
directing the laser beam into the proximal end of the compact laser-steering end effector of claim 1 to a region proximate the distal end of the end effector;
reflecting the laser beam in the region proximate the distal end of the end effector with at least the first and the second active mirrors; and
using actuators to change the tilt orientation of at least the first and the second active mirrors to displace the laser beam across the external target.

14. The method of claim 13, further comprising displacing the laser beam with a third mirror in combination with the at least two active mirrors.

15. The method of claim 14, wherein the third mirror is fixedly mounted.

16. The method of claim 13, wherein the actuators are cantilevers.

17. The method of claim 16, wherein bending of the cantilevers displaces passive linkages coupled with the mirrors to change the tilt of the mirrors.

18. The method of claim 13, wherein the target is a living organism.

19. The method of claim 18, wherein the living organism is a human.

20. The method of claim 19, further comprising excising benign or cancerous lesions in the pharynx and larynx or performing laser-assisted cardiac ablation, laser-assisted surgery of gastrointestinal tract, laser-assisted abdominal surgery, or laser-assisted transnasal skull base surgery in situ in the human via the displacement of the laser beam by the mirrors.

* * * * *